United States Patent [19]

Hasebe et al.

[11] Patent Number: 5,728,649
[45] Date of Patent: Mar. 17, 1998

[54] AGRICULTURAL CHEMICAL COMPOSITION

[75] Inventors: Keiko Hasebe; Yuichi Hioki; Osamu Tachizawa; Takeshi Tomifuji; Tohru Katoh; Uichiro Nishimoto; Yoshifumi Nishimoto; Kohshiro Sotoya, all of Wakayama, Japan

[73] Assignee: Kao Corporation, Tokyo, Japan

[21] Appl. No.: 467,826

[22] Filed: Jun. 6, 1995

Related U.S. Application Data

[62] Division of Ser. No. 151,169, Nov. 12, 1993, abandoned.

[30] Foreign Application Priority Data

Nov. 13, 1992 [JP] Japan ..................... 4-303978
Nov. 13, 1992 [JP] Japan ..................... 4-303979
Nov. 13, 1992 [JP] Japan ..................... 4-303980

[51] Int. Cl.$^6$ ........................... A01N 25/00; A01N 25/30
[52] U.S. Cl. ........................................ 504/116; 514/788
[58] Field of Search .................... 504/116; 564/197; 514/788

[56] References Cited

U.S. PATENT DOCUMENTS 4,228,042 10/1980 Letton ........................................ 252/528
4,888,049 12/1989 Iwasaki et al. ........................... 71/94

FOREIGN PATENT DOCUMENTS

| 0453086 | 10/1991 | European Pat. Off. . |
| 0509346 | 10/1992 | European Pat. Off. . |
| 2600494 | 12/1987 | France . |
| 4105536 | 8/1992 | Germany . |
| 428745 | 1/1992 | Japan . |

*Primary Examiner*—S. Mark Clardy
*Attorney, Agent, or Firm*—Birch, Stewart, Kolasch & Birch, LLP

[57] ABSTRACT

A method for enhancing an efficacy of an agricultural chemical which comprises incorporating a specific quaternary ammonium enhancer into a diluted solution of the agricultural chemical.

2 Claims, No Drawings

AGRICULTURAL CHEMICAL COMPOSITION

This application is a divisional of application Ser. No. 08/151,169, filed on Nov. 12, 1993, abandoned, the entire contents of which are hereby incorporated by reference.

BACKGROUND OF THE INVENTION

1. Field of the Invention

The present invention relates to a method for enhancing the effectiveness of an agricultural chemical, a novel agricultural chemical composition containing a specific enhancer and a use of an enhancer for the preparation of the agricultural chemical composition.

2. Description of the Related Art

Agricultural chemicals including fungicides (or bactericides), insecticides, herbicides, acaricides (or miticides) and plant growth regulators have been used in the forms of, for example, emulsions, wettable powders, granules, powders and flowables. In the properties of these agricultural chemical preparations, various attempts have been made to achieve the maximum effectiveness of the agricultural chemicals. However, it has been difficult to enhance the effectiveness of agricultural chemicals through adjustments in formulations. It is further difficult to develop novel agricultural chemicals. Therefore, further enhancement of existing agricultural chemicals would highly contribute to the industry.

As substances capable of enhancing agricultural chemicals, surfactants comprising various nitrogen-containing compounds such as quaternary ammonium salts, betaines and amine oxides have been known (see European Patent Publication-A No. 274369, published on Jul. 13, 1988). It is known that quaternized or further polyoxyethylenated long-chain amines, among the above-mentioned compounds, are effective for this purpose. These compounds capable of enhancing agricultural chemicals each contains a halogen ion as a counter ion. Namely, these compounds are halide compounds. However, these compounds are irritative.

DISCLOSURE OF THE INVENTION

SUMMARY OF THE INVENTION

From the viewpoint that agricultural chemicals can be enhanced by the combined use of agricultural chemicals with quaternary ammonium salt compounds, the present inventors have conducted extensive studies. As a result, they have found that specific compounds, among quaternary ammonium salt compounds, are particularly effective in enhancing the effectiveness of various agricultural chemicals, thus completing the present invention.

Thus, the present invention provides an agricultural chemical composition comprising an agricultural chemical and an effective amount for enhancing the effectiveness of the agricultural chemical of an enhancer compound selected from the group consisting of compounds represented by the following general formulae (I) to (III):

$$\begin{array}{c} B \\ | \\ C-N^{\oplus}-C_3H_6-N-A.X^{\ominus} \\ | \qquad\qquad | \\ D \qquad\qquad COR^1 \end{array} \quad (I)$$

wherein

A represents a hydrogen atom, $-CH_2CH_2CN$, $-CH_2CH_2COOH$, $$\begin{array}{c} -CHCOONa \\ | \\ CH_2COONa \end{array}, \quad \begin{array}{c} -C_nH_{2n}O-(CH_2CHO)_p-COR^2 \\ | \\ R \end{array}$$

(wherein n is 2 to 9, p is 0 to 30, R or each of the plural R's is a hydrogen atom or a methyl group and $R^2$ is an alkyl or alkenyl group having 4 to 30 carbon atoms), $-C_mH_{2m}NH-COR^2$ (wherein m is 2 to 9 and $R^2$ is as described above) or $$\begin{array}{c} -C_mH_{2m}O-(CH_2CHO)_p-C_rH_{2r}-NH-COR^2 \\ | \\ R \end{array}$$

(wherein r is 2 to 6 and m, p, R and $R^2$ are described above);

B, C and D are either the same or different from one another and each represents a hydrogen atom, a methyl group, an ethyl group $-(C_iH_{2i}O)_j-COR^3$ (wherein i is 2 to 6, j is 1 to 10 and $R^3$ is an alkyl or alkenyl group having 4 to 30 carbon atoms), $-CH_2COO^{\ominus}$, $-CH_2COOH$, $-(C_iH_{2i}O)_j-H$ (wherein i and j are as described above), $-CH_2CH(OH)CH_2SO_3^{\ominus}$ or $$-CH_2-\langle\!\langle\bigcirc\rangle\!\rangle\ ,$$

with the proviso that only one of B, C and D represents either $-CH_2COO^{\ominus}$ or $-CH_2CH(OH)CH_2SO_3^{\ominus}$ or B, C and D are other than $-CH_2COO^{\ominus}$ and $-CH_2CH(OH)CH_2SO_3^{\ominus}$;

$R^1$ represents an alkyl or alkenyl group having 4 to 30 carbon atoms; and $X^{\ominus}$ represents a counter ion;

with the proviso that when one of B, C and D represents either $-CH_2COO^{\ominus}$ or $-CH_2CH(OH)CH_2SO_3^{\ominus}$, $X^{\ominus}$ should be, deleted from the formula (I), $$\begin{array}{c} H \\ | \\ R^4-N^{\oplus}-Y.X^{\ominus} \\ | \\ Z \end{array} \quad (II)$$

wherein

Y and Z are either the same or different from each other and each represents an alkyl or alkenyl group having 6 to 30 carbon atoms, $$\begin{array}{c} -(CH_2CHO)_p-COR^6 \\ | \\ R^5 \end{array}$$

(wherein p is 0 to 30, $R^5$ or each of the plural $R^5$'s is a hydrogen atom or a methyl group and $R^6$ is an alkyl or alkenyl group having 5 to 29 carbon atoms), $-C_3H_6NHCOR^6$ (wherein $R^6$ is as described above), $-C_3H_6OR^6$ (wherein $R^6$ is as described above), $-CH_2CH(OH)CH_2OR^6$ (wherein $R^6$ is as described above) or $$\begin{array}{c} -C_mH_{2m}O-(CH_2CHO)_p-C_nH_{2n}-NH-COR^6 \\ | \\ R^5 \end{array}$$

(wherein m is 2 to 9, n is 2 to 9 and p, $R^5$ and $R^6$ are described above), with the proviso that Y and Z do not simultaneously represent alkyl and/or alkenyl groups having 6 to 30 carbon atoms;

$R^4$ represents an alkyl group having 1 to 4 carbon atoms or

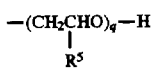

(wherein q is 1 to 30 and $R^5$ is as described above); and $X^\ominus$ represents a counter ion, and

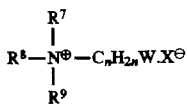 (III)

wherein $R^7$ and $R^8$ are either the same or different from each other and each represents an alkyl group having 1 to 4 carbon atoms, an alkenyl group having 2 to 4 carbon atoms or

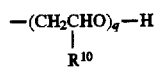

(wherein q is 1 to 30 and $R^{10}$ or each of the plural $R^{10}$'s is a hydrogen atom or a methyl group);

$R^9$ represents an alkyl group having 6 to 36 carbon atoms,

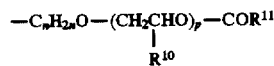

(wherein n is 2 to 9, p is 0 to 30, $R^{11}$ is an alkyl group having 5 to 35 carbon atoms and $R^{10}$ is as described above), $-C_mH_{2m}NH-COR^{11}$ (wherein m is 2 to 9 and $R^{11}$ is as described above) or

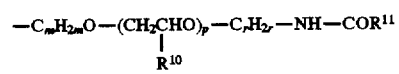

(wherein r is 2 to 6 and m, p, $R^{10}$ and $R^{11}$ are described above);

W represents

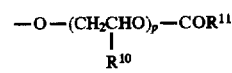

(wherein p, $R^{10}$ and $R^{11}$ are as described above), $-NH-COR^{11}$ (wherein $R^{11}$ is as described above) or

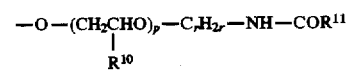

(wherein p, r, $R^{10}$ and $R^{11}$ are as described above);

n is 2 to 9; and $X^\ominus$ is a counter ion.

Examples of the counter ion include a halogen ion such as Cl⁻, Br⁻ or I⁻, an alkylsulfate anion ($RSO_4^-$), an alkylbenzenesulfonic acid anion (R-benzene-($SO_3^-$)), an alkylnaphthalenesulfonic acid anion (R-naphthalene-($SO_3^-$)), a fatty acid anion ($RCOO^-$), an alkylphosphate anion ($ROPO_3H^-$), an anionic oligomer and an anionic polymer. As described above, a counter ion against $N^\oplus$ is $X^\ominus$, or $-CH_2COO^\ominus$ or $-CH_2CH(OH)CH_2SO_3^\ominus$ as the substituent B, C or D in the general formula (I).

Preferable examples of the compounds represented by the above general formula (I) include those represented by the following general formula (Ia):

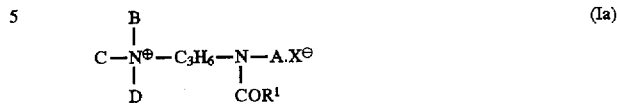 (Ia)

wherein

A represents H, $-CH_2CH_2-CN$, $-CH_2CH_2COOH$,

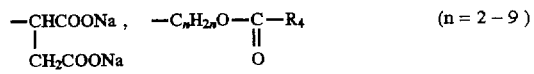 (n = 2 – 9)

or

 (m = 2 – 9);

B, C and D are either the same or different from one another and each represents H, $-CH_3$, $-CH_2CH_3$,

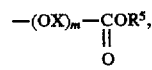

$-CH_2COO^\ominus$, $-CH_2COOH$, $-(C_pH_{2p}O)_q-H$ (p=2–6, q=1–10),

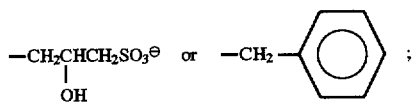

$R^1$ to $R^5$ are either the same or different from one another and each represents an alkyl or alkenyl group having 4 to 30 carbon atoms; and $X^\ominus$ is a counter ion.

Preferable examples of the compounds represented by the above general formula (II) include those represented by the following general formula (IIa):

 (IIa)

wherein

Y and Z are either the same or different from each other and each represents an alkyl group having 6 to 30 carbon atoms or an alkenyl group having 6 to 30 carbon atoms, $-C_2H_4OCOR$, $-C_3H_6NHCOR$, $-C_3H_6OR$ or $-CH_2CH(OH)CH_2OR$ (provided that Y and Z do not simultaneously represent alkyl or alkenyl groups having 6 to 30 carbon atoms);

R represents an alkyl group having 5 to 29 carbon atoms or an alkenyl group having 5 to 29 carbon atoms;

$R^1$ represents an alkyl group having 1 to 4 carbon atoms or a hydroxyalkyl group having 1 to 4 carbon atoms; and $X^\ominus$ is a counter ion.

Preferable examples of the compounds represented by the above general formula (III) include those represented by the following general formula (IIIa):

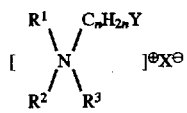

(IIIa):

wherein

R¹ and R² are either the same or different from each other and each represents an alkyl group having 1 to 4 carbon atoms or an alkenyl group having 1 to 4 carbon atoms;

R³ represents an alkyl group having 6 to 36 carbon atoms, —$C_nH_{2m}OCOR^4$ or —$C_mH_{2m}NHCOR^4$ (m=2~9);

R⁴ represents an alkyl group having 5 to 35 carbon atoms;

Y represents —$OCOR^5$ or —$NHCOR^5$;

R⁵ represents an alkyl group having 5 to 35 carbon atoms:

n is 2~9; and $X^\ominus$ is a counter ion.

Further, the present invention provides a method for enhancing the effectiveness of an agricultural chemical which comprises applying an enhancer compound selected from the group consisting of compounds represented by the above general formulae (I) to (III) with an agricultural chemical to a locus which would benefit from such treatment. In this method, the enhancer and the agricultural chemical are generally diluted with water or a liquid carrier.

Examples of the locus or the area to be treated include farm, plantaion, fruit garden, orchard, flower garden, lawn, wood and forest. Examples of the locus include, further, plants, crops such as cereals, vegetables and fruits, trees, fruit trees, grasses, weeds, seeds, fungi, bacteria, insects, acarids and mites.

Furthermore, the present invention provides a use of a compound selected from the group consisting of compounds represented by the above general formulae (I) to (III) for the preparation of an agricultural chemical composition, an enhancer (or an adjuvant) for agricultural chemicals comprising a compound selected from the group consisting of compounds represented by the above general formulae (I) to (III); and a use of the enhancer for enhancing the efficacy of an agricultural chemical.

In addition, the present invention provides an agricultural chemical kit which comprises a container containing the enhancer described above and a container containing an agricultural chemical composition; another agricultural chemical kit which comprises a container containing the enhancer described above and a surfactant other than the compounds represented by the above formulae (I) to (III) and a container containing an agricultural chemical composition; and another agricultural chemical kit which comprises a container containing the enhancer described above, a container containing a surfactant other than the compounds represented by the above formulae (I) to (III) and a container containing an agricultural chemical composition.

In this specification, the term "agricultural chemical" means one which is employed as an active or principle ingredient in common agricultural chemical compositions or preparations, and examples thereof include a fungicide (or a bactericide), an insecticide, an acaricide (or a miticide), a herbicide, a plant growth regulator and the like.

Further the scope and the applicability of the present invention will become apparent from the detailed description given hereinafter. However, it should be understood that the detailed description and specific examples which follow, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

In the present invention, compounds represented by the above general formulae (I), (II) or (III) are used as enhancers for agricultural chemicals.

Among the compounds represented by the above general formula (I), those wherein A represents —$C_nH_{2n}O$—$COR^2$ or —$C_mH_{2m}NH$—$COR^2$ (wherein R² is an alkyl or alkenyl group having 10 to 30 carbon atoms) and B, C and D are each a hydrogen atom or a methyl group may be cited as particularly suitable.

The compound of the general formula (I) according to the present invention can be obtained by, for example, reacting an N,N-dialkylaminoalkylamine with a nitrile compound, hydrogenating the obtained product to give a triamine, reacting the triamine thus obtained with a fatty acid to thereby give a diamide amine and then quaternizing this diamide amine with, for example, an alkyl chloride. Needless to say, the method for the preparation of the compound of the general formula (I) according to the present invention is not restricted thereto.

Among the compounds represented by the general formula (II), those wherein R⁴ is an alkyl group having 1 to 4 carbon atoms, and either Y or Z is a group having an ester bond or an amido group and another is an alkyl group may be cited as particularly suitable.

The compound of the general formula (II) according to the present invention can be obtained by, for example, reacting the corresponding secondary amine with an epoxy compound or a halo alcohol to thereby give an amino alcohol and esterifying this amino alcohol with a fatty acid or a fatty acid ester to thereby give the ester amine of the present invention. Alternatively, the amide amine of the present invention can be obtained by allowing the corresponding secondary amine and acrylonitrile to undergo an addition reaction and hydrogenating, followed by the amidation of the amine thus obtained with a fatty acid or a fatty acid ester. Needless to say, the method for the preparation of the compound of the general formula (II) according to the present invention is not restricted thereto.

Among the compounds represented by the general formula (III), the compound represented by the following formula is particularly preferable:

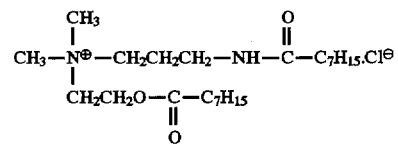

The compound of the general formula (III) according to the present invention is prepared by, for example, cyanoethylating an N-(lower alkyl)alkanolamine, hydrogenating the reaction produce, condensing the corresponding tertiary amine thus obtained with a fatty acid and quaternizing it in a conventional manner. Alternatively, the compound of the general formula (III) can be prepared by condensing N,N-dimethylpropanediamine with a fatty acid and then quaternizing it with an alkyl halide. Needless to say, the method for the preparation of the compound of the general formula (III) according to the present invention is not restricted thereto.

When used together with an agricultural chemical, the enhancer for agricultural chemicals according to the present invention, i.e., the compound represented by the above general formulae (I), (II) or (III), can enhance the effectiveness of the agricultural chemical twice or thrice without causing any chemical injury. Namely, the enhancer for agricultural chemicals of the present invention can be safely applied to various crops without causing any chemical injury.

It has nor necessarily been clarified why the enhancer for agricultural chemicals comprising the compound of the general formula (I), (II) or (III) according to the present invention exerts a remarkable enhancement effect regardless of the type of the structure of the agricultural chemical. One of the reasons therefor seemingly resides in that the enhancer of the present invention exerts a very strong solubilizing power on an agricultural chemical and, therefore, promotes the penetration of the agricultural chemical into the surfaces of plants, insects, fungi or bacteria.

The combined use of at least one compound selected from the group consisting of the compounds represented by the general formulae (I) to (III) according to the present invention with surfactant(s) other than these compounds makes it possible to reduce the dose of the compound(s) represented by the general formulae (I) to (III) while maintaining their enhancement effect on agricultural chemicals. Namely, the present invention also relates to an enhancer (or an enhancer composition) comprising a compound represented by the general formulae (I), (II) or (III) and a surfactant other than compounds represented by the general formulae (I), (II) or (III).

As surfactants other than the compounds represented by the general formulae (I) to (III), nonionic surfactants, anionic surfactants, cationic surfactants, ampholytic surfactants and mixtures of two or more surfactants described above are useful.

Examples of the nonionic surfactants include polyoxyethylene alkyl ethers, polyoxyethylene alkylaryl ethers, polyoxyethylene alkylaryl ether/formaldehyde condensates, polyoxyalkylene aryl ethers, polyoxyalkylene alkyl esters, polyoxyalkylene alkylsorbitol esters, polyoxyalkylene sorbitan esters, polyoxyalkylene alkylglycerol esters, polyoxyalkylene block copolymers, polyoxyalkylene block copolymer/alkylglycerol esters, polyoxyalkylene alkylsulfonamides, polyoxyalkylene rosin esters, polyoxypropylene block copolymers, polyoxyethylene oleyl ether, polyoxyalkylene alkylphenols and mixtures comprising two or more of these surfactants.

Examples of the cationic surfactants include alkylamine/ ethylene oxide adducts and alkylamine/propylene oxide adducts such as tallow amine/ethylene oxide adduct, oleylamine/ethylene oxide adduct, soy amine/ethylene oxide adduct, coco amine/ethylene oxide adduct, synthetic alkylamine/ethylene oxide adducts, octylamine/ethylene oxide adduct and mixtures thereof.

Among anionic surfactants, typical ones are available in the form of an aqueous solution or a solid. Examples thereof include sodium mono- and di-alkylnaphthalenesulfonates, sodium α-olefinsulfonate, sodium alkanesulfonates, alkylsulfates, polyoxyalkylene alkyl ether sulfates, polyoxyalkylene alkyl aryl ether sulfates, polyoxyalkylene styryl phenyl ether sulfates, mono- and dialkylbenzenesulfates, alkylnaphthalenesulfates, alkylnaphthalenesulfonate/ formaldehyde condensates, alkyl diphenyl ether sulfonates, olefinic sulfonates, alkylphosphates, polyoxyalkylene alkylphosphates, polyoxyalkylene phenyl ether phosphates, polyoxyalkyl phenol phosphates, polycarboxylic acid salts, fatty acid salts, stearic acid and its salts, oleic acid and its salts, N-methyl fatty acid taurides and mixtures comprising two or more of these surfactants (including sodium, potassium, ammonium and amine salts).

Examples of suitable ampholytic surfactants include lauryldimethylamine oxide, Armox C/12, amine oxides, Monaterics, Miranols, betaine, Lonzaines, other amine oxides and mixtures thereof.

Among these surfactants, nonionic surfactants are particularly preferable. Still preferable surfactants include those of the ester type, such as polyoxyalkylene sorbitan esters and polyoxyalkylene alkyl glycerol esters, polyoxyalkylene alkyl ethers and polyoxyalkylene alkylnonyl phenols.

In an enhancer (or an enhancer composition) for agricultural chemicals comprising the compound(s) represented by the general formulae (I) to (III) and surfactant(s) other than said compounds, The weight ratio of the content of the compound(s) of the general formulae (I) to (III) to the content of the surfactant(s), i.e., [the (total) content of the compound(s) of the general formulae (I) to (III)/the (total) content of the surfactant(s) other than said compounds], preferably ranges from 1/10 to 50/1, still preferably from 1/1 to 10/1.

The agricultural chemical composition of the present invention comprises the above-mentioned enhancer and an agricultural chemical.

In the agricultural chemical composition comprising the enhancer and an agricultural chemical according to the present invention, it is necessary to use the compound(s) represented by the general formulae (I) to (III), i.e., the enhancer, in an amount wherein the ratio of the (total) content of the compound(s) of the general formulae (I) to (III)/the (total) content of the agricultural chemical(s) is from 0.05 to 50, preferably from 0.05 to 20 and still preferably from 0.1 to 10. When this ratio is below 0.05, any desired effect of enhancing the effectiveness of the agricultural chemical(s) can be fully achieved. When this ratio exceeds 50, on the other hand, the enhancing effect is no longer improved.

Next, examples of the agricultural chemicals to be used in the agricultural chemical composition of the present invention will be cited, though the present invention is not restricted thereto.

In the case of fungicides (or bactericides), included are Dithane or Dipher [zinc ethylenebis(dithiocarbamate)], Magneb or Maneb-dithane [manganese ethylenebis (dithiocarbamate)], Thiram or Thiram 80 [bis (dimehtylthiocarbamoyl)disulfide], Mancozeb [complex of zinc and manganese ethylenebis(dithiocarbamate)], Bis-Dithane [dizinc bis(dimethyldithiocarbamate)ethylenebis (dithiocarbamate)], Propineb or Antracol [polymeric zinc propylenebis(dithiocarbamate)], benzimidazole fungicides such as Benomyl or Benlate [methyl 1-(butylcarbamoyl)-2-benzimidazolecarbamate] and Thiophanate-methyl or Topsin M [1,2-bis(3-methoxycarbonyl-2-thioureido)benzene], Vinclozolin or Ronilan [3-(3,5-dichlorophenyl)-5-methyl-5-vinyl-1,3-oxazolidine-2,4-dione], Iprodione or Rovral [3-(3, 5-dichlorophenyl)-N-isopropyl-2,4-dioxoimidazolidine-1-carboxamide], Procymidone or Sumilex [N-(3,5-dichlorophenyl)-1,2-dimethylcyclopropane-1,2-dicarboximide], Triazine [2,4-dichloro-6-(2-chloroanilino)-1,3,5-triazine], Triflumizole or Trifmine [(E)-4-chloro-α,α, α-trifluoro-N-(1-imidazol-1-yl-2-propoxyethylidene)-o-toluidine], Metalaxyl or Ridomil [methyl-N-(2-methoxyacetyl)-N-(2,6-xylyl)-D,L-alaninate], Bitertanol or Baycoral [all-rac-1-(biphenyl-4-yloxy)-3,3-dimethyl-1-(1H-1,2,4-triazol-1-yl)-2-butan-2-ol], Triadimefon or Bayleton [1-(4-chlorophenoxy)-3,3-dimethyl-1-(1,2,4-triazol-1-yl)-2- butanone], Isoprothiolane or Fuji-one (diisopropyl 1,3-dithiolan-2-ylidenemalonate), Daconil (tetrachloroisophthalonitrile), Pansoil (5-ethoxy-3-trichloromethyl-1,2,4-thiadiazole), Rabcide (4,5,6,7-tetrachlorophthalide), Kitazin P (O,O-diisopropyl S-benzyl thiophosphate), Hinosan (O-ethyl S,S-diphenyl dithiophosphate), Probenazol or Oryzemate (3-allyloxy-1,2-benzisothiazole 1,1-dioxide) and Captan or Orthocide (N-trichloromethylthiotetrahydrophthalimide).

In the case of insecticides, included are pyrethroid insecticides such as Fenvalerate or Vegiphon [α-cyano-3-phenoxybenzyl 2-(4-chlorophenyl)-3-methylbutanoate] and Baythroid [α-cyano-4-fluoro-3-phenoxyphenylmethyl 3-(2,2-dichloroethenyl)-2,2-dimethylcyclcopropanecarboxylate], organophosphorus insecticides such as DDVP or Des (dimethyl 2,2-dichlorovinyl phosphate), Sumithion [O,O-dimethyl O-(3-methyl-4-nitrophenyl)thiophosphate], Malathon or Malathion (S-[1,2-bis(ethoxycarbonyl)ethyl] dimethyl phosphorothionate), Dimethoate [dimethyl S-(N-methylcarbamoylmethyl)dithiophosphate], Elsan or Papthion (S-[α-(ethoxycarbonyl)benzyl]dimethyl phosphorothiolthionate) and Baycid [O,O-dimethyl O-(3-methyl-4-methylthiophenyl)thiophosphate], carbamate insecticides such as Bassa (o-sec-butylphenyl methylcarbamate), MTMC or Tsumacide (m-tolyl methylcarbamate), Meobal (3,4-dimethylphenyl N-methylcarbamate) and NAC or Papnac (1-naphthyl N-methylcarbamate), Methomyl or Lannate (S-methyl-N-[(methylcarbamoyl)oxy]thioacetimidate) and Cartap or Padan [1,3-bis(carbamoylthio)-2-(N,N-dimethylamino) propane hydrochloride].

In the case of acaricides (or miticides), included are Sunmite [2-tert-butyl-5-(4-tert-butylbenzylthio)-4-chloropyridazin-8(2H)-one], Acricid (2,4-dinitro-6-sec-butylphenyldimethylacrylate], Chloromite (isopropyl 4,4-dichlorobenzylate), Akar (ethyl 4,4-dichlorobenzilate), Kelthane [1,1-bis-(p-chlorophenyl)-2,2,2-trichloroethanol], Citrazon (ethyl O-benzoyl-3-chloro-2,6-dimethoxybenzohydroximate), Omite [2-(p-tert-butylphenoxy)cyclohexyl 2-propynyl sulfite], Osadan [hexakis(β,β-dimethylphenylethyl)distannoxane], Hexythiazox or Nissorun [trans-5-(4-chlorophenyl)-N-cyclohexyl-4-methyl-2-oxo-thiazolidine-3-carboxamide] and Amitraz or Dani-Cut [3-methyl-1,5-bis(2,4-xylyl)-1,3,5-triazapenta-1,4-diene].

In the case of herbicides, included are acid amide herbicides such as Stam (3',4'-dichloropropionanilide, DCPA) and Dacklone (3-chloro-2-methyl-p-valerotoluidide, CMMP), urea herbicides such as DCMU or Karmex [3-(3,4-dichlorophenyl)-1,1-dimethylurea] and Linuron [3-(3,4-dichlorophenyl)-1-methoxy-1-methylurea), dipyridyl herbicides such as Paraquat (1,1'-dimethyl 4,4'-bipyridinium dichloride) and Diquat (6,7-dihydrodipyrido[1,2-a:2',1'-c] pyrazindiium dibromide), diazine herbicides such as Bromacil (5-bromo-3-sec-butyl-6-methyluracil), S-triazine herbicides such as Simazine [2-chloro-4,6-bis(ethylamino)-1,3,5-triazine] and Simetryne [2,4-bis(ethylamino)-6-methylthio-1,3,5-triazine], nitrile herbicides such as DBN (2,6-dichlorobenzonitrile), dinitroaniline herbicides such as Trifluralin (α,α,α-trifluoro-2,6-dinitro-N,N-dipropyl-p-toluidine), carbamate herbicides such as Benthiocarb or Saturn [S-(p-chlorobenzyl) N,N-diethylthiolcarbamate] and MCC (methyl 3,4-dichlorocarbanilate), diphenylether herbicides such as NIP (2,4-dichlorophenyl-p-nitrophenylether), phenol herbicides such as PCP (sodium pentachloro-phenoxide), benzoic acid herbicides such as MDBA (dimethylamine-3,6-dichloro-o-anisate), phenoxy herbicides such as sodium 2,4-D (sodium 2,4-dichlorophenoxyacetate) and Mapica ([(4-chloro-o-toluyl) oxy]-aceto-o-chloroanilide), organic phosphorus herbicides such as Glyphosate [N-(phosphonomethyl)-glycine] and salts thereof, Bialaphos or Herbiace (sodium sale of L-2-amino-4-[(hydroxy)(methyl)=(phosphinoyl)]butyryl-L-alanyl-L-alanine) and Glufosinate or Basra [ammonium DL-homoalanin-4-yl (methyl)phosphinate], and aliphatic herbicides such as sodium TCA (sodium trichloroacetate).

In the case of plant growth regulators, included are MH (maleic hydrazide), Ethrel (2-chloroethylphosphonic acid), UASTA and Bialaphos or Herbiace.

The agricultural chemical composition of the present invention may be formulated into any preparation such as emulsions, wettable powders, granules powders or flowables without any limitation. Accordingly, said composition may contain other additives which are selected depending on the formulation, for example, emulsifiers, dispersing agents and carriers.

The agricultural chemical composition according to the present invention may further contain a chelating agent, a pH regulator, an inorganic salt or a thickener, if required.

Examples of chelating agents include aminopolycarboxylic acid type chelating agents, aromatic or aliphatic carboxylic acid type chelating agents, amino acid type chelating agents, ether polycarboxylic acid type chelating agents, iminodimethylphosphonic acid (IDP), dimethylglyoxime (DG) and alkyldiphosphonic acids (ADPA). These chelating agents are as such or in the form of salts (sodium, potassium or ammonium salt) thereof.

Examples of the aminopolycarboxylic acid type chelating agents include a) compounds represented by the chemical formula of $RNX_2$, b) compounds represented by the chemical formula of $NX_3$, c) compounds represented by the chemical formula of $R—NX—CH_2CH_2—NX—R$, d) compounds represented by the chemical formula of $R—NX—CH_2CH_2—NX_2$, e) compounds represented by the chemical formula of $X_2N—R'—NX_2$ and f) compounds similar to compounds of e) and containing four or more X's, for example, a compound represented by the formula:

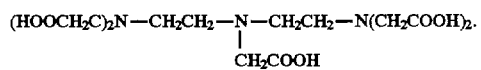

In the above formulae, X represents —CH$_2$COOH or —CH$_2$CH$_2$COOH, R represents a group to be contained in these type, known chelating agents such as a hydrogen atom, an alkyl group, a hydroxy group and a hydroxyalkyl group, and R' represents a group to be contained in these type, known chelating agents such as an alkylene group and a cycloalkylene group.

Representative examples of the aminopolycarboxylic acid type chelating agents include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl) ethylenediaminetriacetic acid (EDTA-OH) and glycoletherdiaminetetraacetic acid (GEDTA), and salts thereof.

Examples of the aromatic or aliphatic carboxylic acid type chelating agents to be used in the present invention include citric acid, oxalic acid, glycolic acid, pyruvic acid and anthranilic acid, and salts thereof. Further, examples of the amino acid type chelating agents to be used in the present invention include glycine, serine, alanine, lysine, cystine, cysteine, ethionine, tyrosine and methionine, and salts and derivatives thereof.

Furthermore, examples of the ether polycarboxylic acid type chelating agents include compounds represented by the following formula, compounds similar to the compounds represented by the following formula and salts (e.g., sodium salt) thereof:

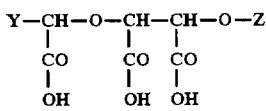

wherein Y represents a hydrogen atom, —$CH_2COOH$ or —COOH, and Z represents a hydrogen atom, —$CH_2COOH$ or

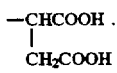

Examples of the pH regulators to be used in the present invention include citric acid, phosphoric acid (e.g., pyrophosphoric acid) and gluconic acid, and salts thereof.

Examples of the inorganic acid salts to be used in the present invention include inorganic mineral salts such as inorganic salts of clay, talc, bentonite, zeolite, calcium carbonate, diatomaceous earth and white carbon, and inorganic ammonium salts such as ammonium sulfate, ammonium nitrate, ammonium phosphate, ammonium thiocyanate, ammonium chloride and ammonium sulfamate.

In addition, examples of thickeners to be used in the present invention include natural, semisynthetic and synthetic, water-soluble thickeners. As natural mucilaginous matters, xanthane gum and zanflow, which are derived from microorganism, and pectine, gum arabic and guar gum, which are derived from plant, are cited. As semisynthetic mucilaginous matters, methylated, carboxyalkylated and hydroxyalkylated products of cellulose such as methylcellulose, carboxymethylcellulose and hydroxymethylcellulose, methylated, carboxyalkylated and hydroxyalkylated products of starch derivatives, and sorbitol are cited. Furthermore, polyacrylates, polymaleates, polyvinylpyrrolidone and pentaerythritol/ethyleneoxide adducts are cited as synthetic mucilaginous matters.

The agricultural chemical composition of the present invention may further contain one or more ingredients such as plant growth regulators other than those cited above, fertilizers and preservatives.

The agricultural chemical composition of the present invention is used in order to control fungi (or bacteria), insects, acarids (or mites) and herbs or to regulate the growth of plants.

The agricultural chemical kit according to the present invention comprises a container containing the enhancer according to the present invention and another container containing an agricultural chemical composition. In this case, the enhancer may comprise at least one compound represented by the above general formulae (I) to (III), or a mixture of at least one compound represented by the above general formulae (I) to (III) and at lease one surfactant other than the compounds represented by the above general formulae (I) to (III). Alternatively, another agricultural chemical kit according to the present invention comprises a container containing at least one compound represented by the above general formulae (I) to (III), a container containing at least one surfactant other than the compounds represented by the above general formulae (I) to (III) and a container containing an agricultural chemical composition.

The "agricultural chemical composition" which is a constituent of the kit is a composition which comprises an agricultural chemical(s), is free from the compounds represented by the above general formulae (I) to (III) and is in the form of, for example, an emulsion or a wettable powder.

In the agricultural chemical kit according to the present invention, a composition comprising an agricultural chemical is separated from the compounds represented by the above general formulae (I) to (III). Namely, the kit differs from an agricultural chemical composition comprising the enhancer for agricultural chemicals and an agricultural chemical(s) in admixture.

Each of contents in these containers is not restricted in their form but appropriately prepared depending on the use and purpose. The material of the container is not restricted so long as it is not react with or affect the content. Examples of the material include plastics, glass, foil, etc.

The enhancer according to the present invention is applied with an agricultural chemical to a locus which would benefit from such treatment, i.e., the application of the enhancer and the agricultural chemical. In general, the enhancer and the agricultural chemical are used with water or a liquid carrier. As means for applying the enhancer for agricultural chemicals according to the present invention, (1) one wherein an agricultural chemical composition of the present invention containing the enhancer and having a preparation form is used (if necessary, the agricultural chemical composition is diluted with, for example, tap water), (2) another one wherein an enhancer is added to an agricultural chemical composition, which has been diluted with water, and (3) another one wherein an enhancer is diluted with water and then an agricultural chemical composition is diluted with the resultant diluted enhancer solution, are useful. The desired enhancement effect can be achieved by either means.

The agricultural chemical composition of the present invention includes one containing the agricultural chemical in high concentration and the enhancer in high concentration, and another one containing the agricultural chemical in an appropriate concentration for application and the enhancer in an appropriate concentration for application. When the former is used, the agricultural chemical composition is diluted with water, etc., for example, just before applying. On the other hand, the agricultural chemical compositions used in the above cases (2) and (3) include those containing the agricultural chemical in high concentration and being free from the enhancer of the present invention.

The contents of the agricultural chemical and the enhancer in their diluted solution are not limited. The content of the agricultural chemical in its diluted solution depends on, for example, the kind of the agricultural chemical and its use. While the content of the enhancer in its diluted solution depends on, for example, the kind of the agricultural chemical to be mixed.

The diluted liquid comprising an appropriate amount of an agricultural chemical and an appropriate amount of an enhancer of the present invention is applied to, for example, plants, crops, vegetables, fruits, trees, fruit trees, grasses, weeds or seeds, and, at the same time, to fungi, bacteria, insects, acarids or mites. In other words, the diluted liquid is applied to a farm, a plantain, a fruit garden, an orchard, a flower garden, a lawn, a wood and a forest.

EXAMPLES

The present invention will now be described in more detail with reference to the following Examples which should not be considered to limit the scope of the present invention.

Production Example 1

(a) A four-neck flask provided with a stirrer, a thermometer and a dropping funnel was charged with 204 g of N,N-dimethylaminopropylamine and 106 g of acrylonitrile was added dropwise therein over 1 hour while maintaining the liquid temperature at 60° C. After the completion of the addition, the mixture was aged, i.e., maintained, at the same temperature for 5 hours. After the completion of the aging, the reaction mixture was transferred into an autoclave equipped with a stirrer, a thermometer and a pressure gauge. Next, 30 g of Raney nickel was added thereto and hydrogenation was effected over 6 hours while maintaining the hydrogen pressure at 20 kg/cm$^2$ G. After the completion of the reaction, the Raney nickel was filtered off and the reaction mixture was distilled to thereby give 180 g of a triamine. The boiling point of this product was 86° C./0.2 mmHg.

(b) A four-neck flask provided with a stirrer, a thermometer and a dropping funnel was charged with 78 g of the triamine obtained above and 285 g of octadecanoic acid and heated to 150° C. Then amidation was effected at the same temperature for 12 hours while distilling off the water thus formed to thereby give 350 g of the target diamide amine. Based on the NMR and IR spectra, it was confirmed that this diamide amine had the following structure:

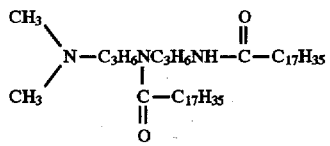

(c) Subsequently, the diamide amine obtained above was quaternized with methyl chloride in a conventional manner and thus the following compound (hereinafter referred to as "enhancer 1") was obtained.

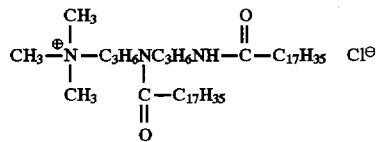

Example 1

The enhancer 1 obtained in the above Production Example 1 was dissolved in deionized water so as to give a 0.2% by weight solution. By using this 0.2% by weight solution, commercially available herbicides, i.e., a Roundup liquid formulation (content of the active ingredient, i.e., isopropylamine salt of Glyphosate: 41% by weight), a Karmex wettable powder (content of the active ingredient. i.e., DCMU: 78.5% by weight) and a Herbiace water-soluble powder (content of the active ingredient, i.e., Bialaphos: 20% by weight) were each diluted 300-fold. Thus, three agricultural chemical compositions of the present invention which contain the same enhancer were obtained.

Rich soil obtained from a paddy field, gravels and a culture soil available on the market were mixed one another at the weight ratio of 7:2:1. Pots having an inside diameter of 12 cm were filled with the soil thus obtained. In order to conduct a glasshouse-test, the seeds of crabgrass were sowed in the pots and germinated. The pots wherein the growth of the crabgrass was abnormal were abandoned to reduce the irregularity among pots. The pots wherein crabgrasses had been grown at a height of about 18 cm were used in the test. Spray gun (mf. by Iwata Tosoki Kogyo K.K., type RG) was used for the application of the agricultural chemical compositions to the crabgrasses. The crabgrasses in the pots were uniformly sprayed with each of the agricultural chemical compositions at a ratio corresponding to 10 l/a (liter per are) to evaluate the herbicidal efficacy.

On the tenth day after the application, the above-ground part of the fresh plant was weighed and the result was expressed in a herbicidal percentage on the basis of the fresh weight of the above-ground part in the untreated lot (see the following formula).

$$\text{Herbicidal ratio} = \frac{\text{(above-ground fresh weight of control lot)} - \text{(above-ground fresh weight of test lot)}}{\text{(above-ground fresh weight of control lot)}} \times 100(\%)$$

The above procedure was repeated except that the enhancer 1 was replaced by the following enhancers 2 to 24 to thereby give agricultural chemical compositions and the herbicidal efficacy of each composition was evaluated. Further, each agricultural chemical was used alone without adding any enhancer and the herbicidal efficacy was evaluated in the same manner. Namely, 3 agricultural chemical compositions which were prepared by diluting one of the above-described commercially available herbicides 300-fold with deionized water were also evaluated. Table 1 summarizes the results.

Enhancer 2; enhancer 1/Emulgen 909 [POE(9) nonyl phenol ether]=80/20.

Enhancer 3; enhancer 1/Emulgen 103 [POE(3) $C_{12}H_{25}OH$]=80/20.

Enhancer 4; enhancer 1/Emanon 4110 [POE(10) $C_{17}H_{35}COOH$]=80/20.

Enhancer 5; enhancer 1/Rheodol TWL-120 [POE(20) $C_{11}H_{23}COO$ sorbitan ester]=80/20.

Enhancer 6; a compound represented by the following formula was used:

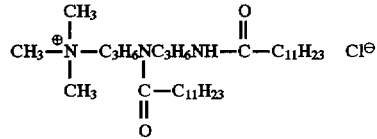

Enhancer 7: enhancer 8/Emulgen 703 [a mixture of POE (3) $C_{12}H_{25}OH$ and POE(3) $C_{13}H_{27}OH$]=75/25.

Enhancer 8; enhancer 6/Emanon 1112 [POE(12) $C_{11}H_{23}COOH$]=75/25.

Enhancer 9; enhancer 6/Rheodol TWL-120 [POE(20) $C_{17}H_{33}COO$ sorbitan ester]=75/25.

Enhancer 10; didecyldimethylammonium chloride.

Enhancer 11; monolauryltrimethylammonium chloride.

Enhancer 12; dilauryldihydroxyethylammonium chloride.

Enhancer 13; trimethylcocoammonium chloride.

Enhancer 14; a compound represented by the following formula was used:

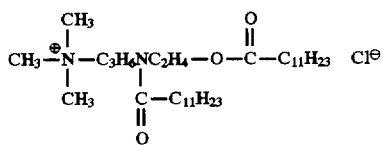

Enhancer 15; enhancer 14/Emulgen 909=80/20.

Enhancer 16; enhancer 14/Emulgen 103=80/20.

Enhancer 17; enhancer 14/Emanon 4110=80/20.

Enhancer 18; enhancer 14/Rheodol TWO-120=80/20.

Enhancer 19; a compound represented by the following formula was used:

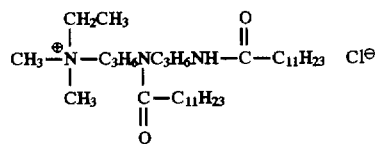

Enhancer 20; enhancer 19/Emulgen 703=75/25.

Enhancer 21; enhancer 19/Emanon 1112=75/25.

Enhancer 22; enhancer 19/Rheodol TWO-120=75/25.

Enhancer 23; a compound represented by the following formula was used:

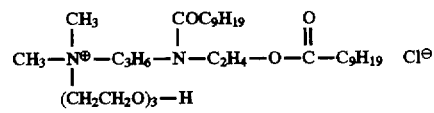

Enhancer 24; enhancer 23/Rheodol TWO-120=80/20.

The express on "POE" as used herein is an abbreviation of "polyoxyethylene" and each value given in the parentheses is an average addition mole number of oxyethylene. In the above-described enhancers, the composition ratio is by weight.

TABLE 1

| | Herbicidal ratio (%) | | |
|---|---|---|---|
| No. of enhancer | Karmex wettable powder | Herbiace water-soluble powder | Roundup liquid formulation |
| Invention product | | | |
| 1 | 98.5 | 98.3 | 99.4 |
| 2 | 99.3 | 98.3 | 99.5 |
| 3 | 98.0 | 97.9 | 98.1 |
| 4 | 97.8 | 98.9 | 99.2 |
| 5 | 97.8 | 99.1 | 98.2 |
| 6 | 98.6 | 98.8 | 98.8 |
| 7 | 99.4 | 99.4 | 99.0 |
| 8 | 99.0 | 99.3 | 99.2 |
| 9 | 98.9 | 98.2 | 99.3 |
| Comparative product | | | |
| 10 | 63.5 | 70.0 | 73.5 |
| 11 | 44.5 | 72.2 | 76.1 |
| 12 | 60.3 | 70.1 | 71.1 |
| 13 | 50.3 | 65.8 | 75.3 |

TABLE 1-continued

| | Herbicidal ratio (%) | | |
|---|---|---|---|
| No. of enhancer | Karmex wettable powder | Herbiace water-soluble powder | Roundup liquid formulation |
| Invention product | | | |
| 14 | 98.5 | 98.7 | 98.7 |
| 15 | 98.5 | 99.3 | 98.7 |
| 16 | 98.5 | 99.0 | 99.3 |
| 17 | 96.7 | 99.2 | 99.4 |
| 18 | 98.5 | 98.3 | 98.3 |
| 19 | 98.2 | 98.3 | 98.5 |
| 20 | 99.5 | 98.5 | 99.3 |
| 21 | 99.3 | 98.7 | 98.3 |
| 22 | 99.2 | 99.0 | 98.3 |
| 23 | 98.3 | 99.0 | 98.1 |
| 24 | 97.8 | 97.2 | 98.3 |
| none | 18.4 | 67.5 | 68.5 |

Example 2

Female imagines of *Tetranychus kanzawai* Kishida were planted onto kidney bean leaf disks at a ratio of 30 imagines/lot in triplicate runs and incubated at 25° C. for 24 hours. Next, the whole leaf disk was dipped in a test solution for 5 seconds and then taken out of the test solution. After being left to stand at 25° C. for 48 hours, the leaf disk was observed and the acaricidal ratio was determined on the basis of the result in the untreated lot (see the following formula).

$$\text{Miticidal ratio} = \frac{(\text{the number of living acarids of control lot}) - (\text{the number of living acarids of test lot})}{(\text{the number of living acarids of control lot})} \times 100(\%)$$

As an acaricide, a Nissorun V emulsion [content of the active ingredient as an agricultural chemical: 55% by weight (50% by weight of hexythiazox+5% by weight of DDVP)] and an Osadan wettable powder-25 (content of the active ingredient, i.e., fenbutatin oxide: 25% by weight) were each diluted 2,000-fold and used. The same enhancers for agricultural chemicals as those employed in Example 1 were used. Each agricultural chemical composition was prepared in such a manner as to adjust the concentration of the enhancer for agricultural chemicals in the diluted solution to 0.1% by weight. Further, the same procedure was repeated without using any enhancer for agricultural chemicals. Namely, two agricultural chemical compositions which were prepared by diluting one of the above-described commercially available acaricides 2000-fold with deionized water were also evaluated. Table 2 shows the results.

TABLE 2

| No. of enhancer | Acaricidal ratio (%) | |
| --- | --- | --- |
| | Nissorun V emulsion | Osadan wettable powder |
| Invention product | | |
| 1 | 98.8 | 98.8 |
| 2 | 97.8 | 97.8 |
| 3 | 97.8 | 100 |
| 4 | 97.8 | 98.8 |
| 5 | 98.8 | 100 |
| 6 | 100 | 98.8 |
| 7 | 98.8 | 97.8 |
| 8 | 100 | 100 |
| 9 | 100 | 99.2 |
| Comparative product | | |
| 10 | 50.0 | 52.2 |
| 11 | 50.0 | 46.5 |
| 12 | 48.9 | 52.2 |
| 13 | 50.0 | 74.4 |
| Invention product | | |
| 14 | 97.8 | 97.8 |
| 15 | 97.8 | 98.8 |
| 16 | 100 | 100 |
| 17 | 98.8 | 99.2 |
| 18 | 92.2 | 100 |
| 19 | 100 | 100 |
| 20 | 100 | 99.2 |
| 21 | 100 | 100 |
| 22 | 92.2 | 100 |
| 23 | 98.9 | 95.6 |
| 24 | 96.7 | 97.8 |
| none | 44.4 | 38.9 |

Example 3

Rice insect larvae at the third instar were incubated and used in an efficacy test on insecticides in triplicate runs by the dipping method (each lot having 10 larvae). The insecticidal ratio was determined in the same manner as the one employed for the determination of the acaricidal ratio. Marketed insecticides, namely, a Sumithion emulsion (content of the active ingredient, i.e., MEP: 50% by weight) and a Malathion (or Malathon) emulsion (content of the active ingredient, i.e., Malathion: 50% by weight) were each diluted 2,000-fold and used. As enhancers for agricultural chemicals, those employed in Example 1 were used in such a manner as to adjust their concentration in the diluted solution to 0.1% by weight. Table 3 shows the results.

TABLE 3

| No. of enhancer | Insecticidal ratio (%) | |
| --- | --- | --- |
| | Sumithion emulsion | Malathion emulsion |
| Invention product | | |
| 1 | 100 | 90.0 |
| 2 | 100 | 93.3 |
| 3 | 93.3 | 100 |
| 4 | 90.0 | 96.7 |
| 5 | 90.0 | 98.7 |
| 6 | 100 | 100 |
| 7 | 100 | 96.7 |
| 8 | 100 | 96.7 |
| 9 | 100 | 100 |
| Comparative product | | |
| 10 | 60.0 | 50.0 |
| 11 | 50.0 | 53.3 |
| 12 | 53.3 | 60.0 |
| 13 | 40.0 | 43.3 |
| Invention product | | |
| 14 | 100 | 100 |
| 15 | 93.3 | 96.7 |
| 16 | 93.3 | 93.3 |
| 17 | 100 | 100 |
| 18 | 96.7 | 96.7 |
| 19 | 100 | 93.3 |
| 20 | 100 | 100 |
| 21 | 93.3 | 93.3 |
| 22 | 93.3 | 100 |
| 23 | 96.7 | 96.7 |
| 24 | 93.3 | 100 |
| control lot | 40.0 | 50.0 |

Examples 1, 2 and 3 show the tests wherein the efficacies of the enhancers for agricultural chemicals according to the present invention were compared with those of common cationic surfactants (comparative products) as enhancers for agricultural chemicals. As Tables 1 to 3 clearly indicate, the enhancers for agricultural chemicals of the present invention exerted remarkable effects and thus were usable on a practical level. In contrast, the comparative products somewhat enhanced the efficacies of the agricultural chemicals but were not effective on a practical level. Accordingly, it is observed that the enhancers for agricultural chemicals of the present invention would specifically enhance the efficacies of agricultural chemicals as compared with common cationic surfactants.

Example 4

The same test as the one effected in Example 1 was carried out by using a Roundup liquid formulation as a herbicide and the enhancers 1 and 14 listed in Example 1 each in a dose as specified in Table 4. Table 4 shows the results.

TABLE 4

| Test no. | Enhancer | Herbicide content (ppm) | Enhancer content (ppm) | Herbicide/enhancer weight ratio | Herbicidal ratio (%) |
| --- | --- | --- | --- | --- | --- |
| 1 | Enhancer 1 | 2000 | 200 | 1/0.1 | 82.3 |
| 2 | | 2000 | 1000 | 1/0.5 | 97.5 |
| 3 | | 2000 | 2000 | 1/1.0 | 99.1 |
| 4 | | 2000 | 10000 | 1/5 | 99.2 |
| 5 | | 2000 | 24000 | 1/12 | 99.1 |
| 6 | | 2000 | 30000 | 1/15 | 99.3 |
| 7 | | 2000 | 60000 | 1/30 | 99.1 |
| 8 | | 2000 | 0 | | 56.5 |
| 9 | | 0 | 0 | | |
| 10 | Enhancer 14 | 2000 | 200 | 1/0.1 | 78.5 |
| 11 | | 2000 | 1000 | 1/0.5 | 88.5 |

TABLE 4-continued

| Test no. | Enhancer | Herbicide content (ppm) | Enhancer content (ppm) | Herbicide/ enhancer weight ratio | Herbicidal ratio (%) |
|---|---|---|---|---|---|
| 12 | | 2000 | 2000 | 1/1.0 | 92.6 |
| 13 | | 2000 | 10000 | 1/5 | 96.0 |
| 14 | | 2000 | 24000 | 1/12 | 99.2 |
| 15 | | 2000 | 30000 | 1/15 | 99.1 |
| 16 | | 2000 | 60000 | 1/30 | 99.3 |
| 17 | | 2000 | 0 | | 56.5 |
| 18 | | 0 | 0 | | |

Example 5

The same test as the one effected in Example 1 was carried out by using a Roundup liquid formulation as a herbicide and the enhancers 6 and 19 listed in Example 1 each in a dose as specified in Table 5. Table 5 shows the results.

TABLE 5

| Test no. | Enhancer | Herbicide content (ppm) | Enhancer content (ppm) | Herbicide/ enhancer weight ratio | Herbicidal ratio (%) |
|---|---|---|---|---|---|
| 1 | Enhancer 6 | 2000 | 200 | 1/0.1 | 82.1 |
| 2 | | 2000 | 1000 | 1/0.5 | 95.3 |
| 3 | | 2000 | 2000 | 1/1.0 | 98.7 |
| 4 | | 2000 | 10000 | 1/5 | 99.0 |
| 5 | | 2000 | 24000 | 1/12.0 | 98.9 |
| 6 | | 2000 | 60000 | 1/30 | 99.1 |
| 7 | | 2000 | 80000 | 1/40 | 99.1 |
| 8 | | 2000 | 0 | | 56.5 |
| 9 | | 0 | 0 | | |
| 10 | Enhancer 19 | 2000 | 200 | 1/0.1 | 75.4 |
| 11 | | 2000 | 1000 | 1/0.5 | 90.5 |
| 12 | | 2000 | 2000 | 1/1.0 | 93.5 |
| 13 | | 2000 | 10000 | 1/5 | 98.6 |
| 14 | | 2000 | 24000 | 1/12.0 | 99.1 |
| 15 | | 2000 | 60000 | 1/30 | 99.3 |
| 16 | | 2000 | 80000 | 1/40 | 99.1 |
| 17 | | 2000 | 0 | | 56.5 |
| 18 | | 0 | 0 | | |

Example 6

The same test as the one effected in Example 1 was carried out by using a Roundup liquid formulation as a herbicide and the enhancers 2 and 15 listed in Example 1 each in a dose as specified in Table 6. Table 6 shows the results.

TABLE 6

| Test no. | Enhancer | Herbicide content (ppm) | Enhancer content (ppm) | Herbicide/ enhancer weight ratio | Herbicidal ratio (%) |
|---|---|---|---|---|---|
| 1 | Enhancer 2 | 2000 | 200 | 1/0.1 | 81.8 |
| 2 | | 2000 | 1000 | 1/0.5 | 95.4 |
| 3 | | 2000 | 2000 | 1/1.0 | 99.1 |
| 4 | | 2000 | 10000 | 1/5 | 98.9 |
| 5 | | 2000 | 24000 | 1/12 | 99.1 |
| 6 | | 2000 | 30000 | 1/15 | 99.2 |
| 7 | | 2000 | 80000 | 1/40 | 99.1 |
| 8 | | 2000 | 0 | | 56.5 |
| 9 | | 0 | 0 | | |

TABLE 6-continued

| Test no. | Enhancer | Herbicide content (ppm) | Enhancer content (ppm) | Herbicide/ enhancer weight ratio | Herbicidal ratio (%) |
|---|---|---|---|---|---|
| 10 | Enhancer 15 | 2000 | 200 | 1/0.1 | 85.2 |
| 11 | | 2000 | 1000 | 1/0.5 | 96.5 |
| 12 | | 2000 | 2000 | 1/1.0 | 99.4 |
| 13 | | 2000 | 10000 | 1/5 | 99.2 |
| 14 | | 2000 | 24000 | 1/12 | 98.7 |
| 15 | | 2000 | 30000 | 1/15 | 99.3 |
| 16 | | 2000 | 80000 | 1/40 | 99.2 |
| 17 | | 2000 | 0 | | 56.5 |
| 18 | | 0 | 0 | | |

Example 7

The same test as the one effected in Example 3 was carried out by using a Sumithion emulsion as an insecticide and the enhancers 1 and 14 listed in Example 1 each in a dose as specified in Table 7. Table 7 shows the results.

TABLE 7

| Test no | Enhancer | Insecticide content (ppm) | Enhancer content (ppm) | Insecticide/ enhancer weight ratio | Insecticidal ratio (%) |
|---|---|---|---|---|---|
| 1 | Enhancer 1 | 250 | 25 | 1/0.1 | 83.3 |
| 2 | | 250 | 125 | 1/0.5 | 93.3 |
| 3 | | 250 | 250 | 1/1.0 | 100 |
| 4 | | 250 | 500 | 1/2.0 | 100 |
| 5 | | 250 | 1000 | 1/4.0 | 100 |
| 6 | | 250 | 2500 | 1/10 | 100 |
| 7 | | 250 | 5000 | 1/20 | 100 |
| 8 | | 250 | 0 | | 46.7 |
| 9 | | 0 | 0 | | |
| 10 | Enhancer 14 | 250 | 25 | 1/0.1 | 83.3 |
| 11 | | 250 | 125 | 1/0.5 | 90.0 |
| 12 | | 250 | 250 | 1/1.0 | 100 |
| 13 | | 250 | 500 | 1/2.0 | 100 |
| 14 | | 250 | 1000 | 1/4.0 | 100 |
| 15 | | 250 | 2500 | 1/10 | 100 |
| 16 | | 250 | 5000 | 1/20 | 100 |
| 17 | | 250 | 0 | | 46.7 |
| 18 | | 0 | 0 | | |

Example 8

The same test as the one effected in Example 2 was carried out by using an Osadan wettable powder as an acaricide and. the enhancers 5 and 18 listed in Example 1 each in a dose as specified in Table 8. Table 8 shows the results.

TABLE 8

| Test no. | Enhancer | Acaricide content (ppm) | Enhancer content (ppm) | Acaricide/ enhancer weight ratio | Acaricidal ratio (%) |
|---|---|---|---|---|---|
| 1 | Enhancer 5 | 100 | 10 | 1/0.1 | 77.8 |
| 2 | | 100 | 50 | 1/0.5 | 91.1 |
| 3 | | 100 | 100 | 1/1.0 | 100 |
| 4 | | 100 | 200 | 1/2.0 | 100 |
| 5 | | 100 | 1000 | 1/10 | 100 |
| 6 | | 100 | 1500 | 1/15 | 100 |
| 7 | | 100 | 2000 | 1/20 | 100 |
| 8 | | 100 | 0 | | 52.3 |
| 9 | | 0 | 0 | | 2.2 |
| 10 | Enhancer | 100 | 10 | 1/0.1 | 77.8 |

TABLE 8-continued

| Test no. | Enhancer | Acaricide content (ppm) | Enhancer content (ppm) | Acaricide/ enhancer weight ratio | Acaricidal ratio (%) |
|---|---|---|---|---|---|
| 11 | 18 | 100 | 50 | 1/0.5 | 91.1 |
| 12 | | 100 | 100 | 1/1.0 | 100 |
| 13 | | 100 | 200 | 1/2.0 | 100 |
| 14 | | 100 | 1000 | 1/10 | 100 |
| 15 | | 100 | 1500 | 1/15 | 100 |
| 16 | | 100 | 2000 | 1/20 | 100 |
| 17 | | 100 | 0 | | 52.3 |
| 18 | | 0 | 0 | | 2.2 |

Example 9

The same test as the one effected in Example 2 was carried out by using an Osadan wettable powder as an acaricide and the enhancers 7 and 20 listed in Example 1 each in a dose as specified in Table 9. Table 9 shows the results.

TABLE 9

| Test no. | Enhancer | Acaricide content (ppm) | Enhancer content (ppm) | Acaricide/ enhancer weight ratio | Acaricidal ratio (%) |
|---|---|---|---|---|---|
| 1 | Enhancer | 100 | 10 | 1/0.1 | 72.2 |
| 2 | 7 | 100 | 50 | 1/0.5 | 91.1 |
| 3 | | 100 | 100 | 1/1.0 | 100 |
| 4 | | 100 | 200 | 1/2.0 | 100 |
| 5 | | 100 | 1000 | 1/10 | 100 |
| 6 | | 100 | 1500 | 1/15 | 100 |
| 7 | | 100 | 2000 | 1/20 | 100 |
| 8 | | 100 | 0 | | 52.3 |
| 9 | | 0 | 0 | | 2.2 |
| 10 | Enhancer | 100 | 10 | 1/0.1 | 77.8 |
| 11 | 20 | 100 | 50 | 1/0.5 | 94.4 |
| 12 | | 100 | 200 | 1/2.0 | 100 |
| 13 | | 100 | 1000 | 1/10 | 100 |
| 14 | | 100 | 0 | | 52.3 |
| 15 | | 0 | 0 | | 2.2 |

Example 10

The same test as the one effected in Example 1 was carried out by using a Roundup liquid formulation as a herbicide and the enhancers 23 and 24 listed in Example 1 each in a dose as specified in Table 10. Table 10 shows the results.

TABLE 10

| Test no. | Enhancer | Herbicide content (ppm) | Enhancer content (ppm) | Herbicide/ enhancer weight (ppm) | Herbicidal ratio (%) |
|---|---|---|---|---|---|
| 1 | Enhancer | 2000 | 200 | 1/0.1 | 85.6 |
| 2 | 23 | 2000 | 1000 | 1/0.5 | 91.2 |
| 3 | | 2000 | 2000 | 1/1.0 | 98.5 |
| 4 | | 2000 | 10000 | 1/5 | 99.1 |
| 5 | | 2000 | 24000 | 1/12 | 98.3 |
| 6 | | 2000 | 30000 | 1/15 | 98.4 |
| 7 | | 2000 | 60000 | 1/30 | 99.0 |
| 8 | | 2000 | 0 | | 56.5 |
| 9 | | 0 | 0 | | |
| 10 | Enhancer | 2000 | 200 | 1/0.1 | 82.3 |
| 11 | 24 | 2000 | 1000 | 1/0.5 | 88.7 |
| 12 | | 2000 | 2000 | 1/1.0 | 96.8 |
| 13 | | 2000 | 10000 | 1/5 | 97.2 |
| 14 | | 2000 | 24000 | 1/12 | 98.3 |
| 15 | | 2000 | 30000 | 1/15 | 97.7 |
| 16 | | 2000 | 60000 | 1/30 | 98.9 |
| 17 | | 2000 | 0 | | 56.5 |
| 18 | | 0 | 0 | | |

Example 11

The same test as the one effected in Example 2 was carried out by using an Osadan wettable powder as an acaricide and the enhancers 23 and 24 listed in Example 1 each in a dose as specified in Table 11. Table 11 shows the results.

TABLE 11

| Test no. | Enhancer | Acaricide content (ppm) | Enhancer content (ppm) | Acaricide/ enhancer weight ratio | Acaricidal ratio (%) |
|---|---|---|---|---|---|
| 1 | Enhancer | 100 | 10 | 1/0.1 | 90.0 |
| 2 | 23 | 100 | 50 | 1/0.5 | 92.2 |
| 3 | | 100 | 100 | 1/1.0 | 100 |
| 4 | | 100 | 200 | 1/2.0 | 100 |
| 5 | | 100 | 1000 | 1/10 | 100 |
| 6 | | 100 | 1500 | 1/15 | 100 |
| 7 | | 100 | 2000 | 1/20 | 100 |
| 8 | | 100 | 0 | | 52.3 |
| 9 | | 0 | 0 | | 2.2 |
| 10 | Enhancer | 100 | 10 | 1/0.1 | 86.7 |
| 11 | 24 | 100 | 50 | 1/0.5 | 92.2 |
| 12 | | 100 | 100 | 1/1.0 | 100 |
| 13 | | 100 | 200 | 1/2.0 | 100 |
| 14 | | 100 | 1000 | 1/10 | 100 |
| 15 | | 100 | 1500 | 1/15 | 100 |
| 16 | | 100 | 2000 | 1/20 | 100 |
| 17 | | 100 | 0 | | 52.3 |
| 18 | | 0 | 0 | | 2.2 |

Production Example 2

An autoclave provided with a stirrer, a thermometer, a pressure gauge and a pressure dropping funnel was charged with 250 g of N-methyloctadecylamine and heated to 160° C. Then 45 g of ethylene oxide was occasionally added dropwise thereto under a pressure of 0 to 6 kg/cm$^2$ G. Three hours were required for completing the addition. Next, the resulting mixture was aged, i.e., maintained, at 160° C. for 2 hours and then cooled. The reaction mixture was taken out and distilled to thereby give 250 g of N-(2-hydroxyethyl)-N-methyloctadecylamine. This product had a boiling point of 185° to 190° C./0.2 mmHg.

A four-neck flask provided with a stirrer, a thermometer and a dehydrating tube was charged with 200 g of the N-(2-hydroxyethyl)-N-methyloctadecylamine and 174 g of octadecanoic acid. The mixture was heated to 180° C. and maintained at this temperature for 12 hours while distilling off the water thus formed. Thus 350 g of N-(2-octadecanoyloxyethyl)-N-methyloctadecylamine was obtained. Based on the NMR and IR spectra, it was confirmed that this product had the following structure. This compound will be referred to as the enhancer 25 hereinafter.

$$CH_3-\overset{\overset{H}{|}}{\underset{\underset{O}{\underset{\|}{CH_2CH_2OC(CH_2)_{16}CH_3}}}{N^{\oplus}}}-C_{18}H_{37} \quad .Cl^{\ominus}$$

Example 12

The same test as the one effected in Example 1 was carried out, except that the enhancer 25 prepared in Production Example 2 and, the following enhancers 26 to 46 were used to prepare agricultural chemical compositions. Table 12 summarizes the results.

Enhancer 26; enhancer 25/Emulgen 909 [POE(9) nonylphenol ether]=80/20.

Enhancer 27; enhancer 25/Emulgen 103 [POE(3) $C_{12}H_{25}OH$]=80/20.

Enhancer 28; enhancer 25/Emanon 4110 [POE(10) $C_{17}H_{35}COOH$]=80/20.

Enhancer 29; enhancer 25/Rheodol TWL-120 [POE(20) $C_{11}H_{23}COO$ sorbitan ester]=80/20.

Enhancer 30; a compound represented by the following formula was used:

$$CH_3-\overset{\overset{H}{|}}{\underset{\underset{C_{11}H_{23}}{|}}{N^{\oplus}}}-C_2H_4-O-\overset{\overset{}{}}{\underset{\underset{O}{\|}}{C}}-C_{11}H_{23}.Cl^{\ominus}$$

Enhancer 31; enhancer 30/Emulgen 703 [a mixture of POE(3) $C_{12}H_{25}OH$ and POE(3) $C_{13}H_{27}OH$]=75/25.

Enhancer 32; enhancer 30/Emanon 1112 [POE(12) $C_{11}H_{23}COOH$]=75/25.

Enhancer 33; enhancer 30/Rheodol TWO-120 [POE(20) $C_{17}H_{33}COO$ sorbitan ester]=75/25.

Enhancer 34; didecyldimethylammonium chloride.

Enhancer 35; monolauryltrimethylammonium chloride.

Enhancer 36; dilauryldihydroxyethylammonium chloride.

Enhancer 37; trimethylcocoammonium chloride.

Enhancer 38; a compound represented by the following formula was used:

$$CH_3-\overset{\overset{H}{|}}{\underset{\underset{C_{11}H_{23}}{|}}{N^{\oplus}}}-C_3H_6-NH-\overset{\overset{}{}}{\underset{\underset{O}{\|}}{C}}-C_{15}H_{31}.CH_3COO^{\ominus}$$

Enhancer 39; enhancer 38/Emulgen 909=80/20.
Enhancer 40; enhancer 38/Emulgen 103=80/20.
Enhancer 41; enhancer 38/Emanon 4110=80/20.
Enhancer 42; enhancer 38/Rheodol TWO-120=80/20.
Enhancer 43; a compound represented by the following formula was used:

$$CH_3-\overset{\overset{H}{|}}{\underset{\underset{C_{16}H_{33}}{|}}{N^{\oplus}}}-C_3H_6-NH-\overset{\overset{}{}}{\underset{\underset{O}{\|}}{C}}-C_{11}H_{23}.Cl^{\ominus}$$

Enhancer 44; enhancer 43/Emulgen 703=75/25.
Enhancer 45; enhancer 43/Emanon 1112=75/25.
Enhancer 46; enhancer 43/Rheodol TWO-120=75/25.

The express on "POE" as used herein is an abbreviation of "polyoxyethylene" and each value given in the parentheses is an average addition mole number of oxyethylene. In the above-described enhancers, the composition ratio is by weight.

TABLE 12

| No. of enhancer | Herbicidal ratio (%) | | |
|---|---|---|---|
| | Karmex wettable powder | Herbiace water-soluble powder | Roundup liquid formulation |
| Invention product | | | |
| 25 | 98.0 | 98.9 | 99.2 |
| 26 | 98.0 | 98.9 | 99.1 |
| 27 | 99.3 | 99.0 | 99.1 |
| 28 | 99.4 | 99.2 | 97.5 |
| 29 | 99.4 | 99.1 | 99.3 |
| 30 | 98.9 | 98.9 | 99.0 |
| 31 | 99.3 | 99.3 | 97.8 |
| 32 | 99.1 | 99.3 | 99.0 |
| 33 | 99.0 | 99.1 | 99.1 |
| Comparative product | | | |
| 34 | 63.5 | 70.0 | 73.5 |
| 35 | 44.5 | 72.2 | 76.1 |
| 36 | 60.3 | 70.1 | 71.1 |
| 37 | 50.3 | 65.8 | 75.3 |
| Invention product | | | |
| 38 | 98.5 | 98.7 | 99.2 |
| 39 | 98.5 | 99.3 | 99.1 |
| 40 | 98.5 | 99.4 | 98.7 |
| 41 | 96.7 | 99.5 | 98.3 |
| 42 | 98.5 | 98.3 | 98.5 |
| 43 | 99.3 | 98.3 | 99.4 |
| 44 | 99.2 | 98.5 | 99.3 |
| 45 | 99.0 | 99.0 | 99.3 |
| 46 | 99.4 | 99.1 | 99.0 |
| none | 18.4 | 67.5 | 68.5 |

Example 18

The same test as the one effected in Example 2 was carried out, except that the enhancers 25 to 46, which were employed in Example 12, were used to prepare agricultural chemical compositions. Table 13 shows the results.

TABLE 13

| No. of enhancer | Acaricidal ratio (%) | |
|---|---|---|
| | Nissorun V emulsion | Osadan wettable powder |
| Invention product | | |
| 25 | 98.8 | 98.8 |
| 26 | 97.8 | 97.8 |
| 27 | 100 | 97.8 |
| 28 | 100 | 98.8 |
| 29 | 100 | 100 |
| 30 | 98.8 | 100 |
| 31 | 98.8 | 100 |
| 32 | 98.8 | 99.2 |
| 33 | 98.8 | 100 |

TABLE 13-continued

| No. of enhancer | Acaricidal ratio (%) | |
|---|---|---|
| | Nissorun V emulsion | Osadan wettable powder |
| Comparative product | | |
| 34 | 50.0 | 52.2 |
| 35 | 50.0 | 46.5 |
| 36 | 48.9 | 52.2 |
| 37 | 50.0 | 74.4 |
| Invention product | | |
| 38 | 97.8 | 97.8 |
| 39 | 97.8 | 98.8 |
| 40 | 97.8 | 97.8 |
| 41 | 100 | 100 |
| 42 | 98.8 | 100 |
| 43 | 92.2 | 92.2 |
| 44 | 100 | 92.2 |
| 45 | 100 | 100 |
| 46 | 100 | 100 |
| none | 44.4 | 38.9 |

Example 14

The same test as the one effected in Example 3 was carried out, except that the enhancers 25 to 46, which were employed in Example 12, were used to prepare agricultural chemical compositions. Table 14 shows the results.

TABLE 14

| No. of enhancer | Insecticidal ratio (%) | |
|---|---|---|
| | Sumithion emulsion | Malathion emulsion |
| Invention product | | |
| 25 | 90.0 | 100 |
| 26 | 90.0 | 100 |
| 27 | 93.3 | 93.3 |
| 28 | 93.3 | 90.0 |
| 29 | 100 | 100 |
| 30 | 100 | 93.3 |
| 31 | 93.3 | 100 |
| 32 | 100 | 96.7 |
| 33 | 93.3 | 96.7 |
| Comparative product | | |
| 34 | 60.0 | 50.0 |
| 35 | 50.0 | 53.3 |
| 36 | 60.0 | 53.3 |
| 37 | 43.3 | 40.0 |
| Invention product | | |
| 38 | 100 | 96.7 |
| 39 | 93.3 | 93.3 |
| 40 | 96.7 | 100 |
| 41 | 100 | 100 |
| 42 | 96.7 | 100 |
| 43 | 96.7 | 96.7 |
| 44 | 100 | 96.7 |
| 45 | 100 | 93.3 |
| 46 | 93.3 | 93.3 |
| control lot | 40.0 | 50.0 |

Examples 12, 13 and 14 show the tests wherein the efficacies of the enhancers for agricultural chemicals according to the present invention were compared with those of common cationic surfactants (comparative products) as enhancers for agricultural chemicals. As Tables 12 to 14 clearly indicate, the enhancers for agricultural chemicals of the present invention exerted remarkable effects and thus were usable on a practical level. In contrast, the comparative products somewhat enhanced the efficacies of the agricultural chemicals but were not effective on a practical level. Accordingly, it is observed that the enhancers for agricultural chemicals of the present invention would specifically enhance the efficacies of agricultural chemicals as compared with common cationic surfactants.

Example 15

The same test as the one effected in Example 12 was carried out by using a Roundup liquid formulation as a herbicide and the enhancers 25 and 38 listed in Example 12 each in a dose as specified in Table 15. Table 15 shows the results.

TABLE 15

| Test no. | Enhancer | Herbicide content (ppm) | Enhancer content (ppm) | Herbicide/ enhancer weight ratio | Herbicidal ratio (%) |
|---|---|---|---|---|---|
| 1 | Enhancer | 2000 | 200 | 1/0.1 | 82.3 |
| 2 | 25 | 2000 | 1000 | 1/0.5 | 95.6 |
| 3 | | 2000 | 2000 | 1/1.0 | 97.8 |
| 4 | | 2000 | 10000 | 1/5 | 99.0 |
| 5 | | 2000 | 24000 | 1/12 | 98.7 |
| 6 | | 2000 | 30000 | 1/15 | 99.1 |
| 7 | | 2000 | 60000 | 1/30 | 99.0 |
| 8 | | 2000 | 0 | | 56.5 |
| 9 | | 0 | 0 | | 0 |
| 10 | Enhancer | 2000 | 200 | 1/0.1 | 78.5 |
| 11 | 38 | 2000 | 1000 | 1/0.5 | 90.2 |
| 12 | | 2000 | 2000 | 1/1.0 | 95.6 |
| 13 | | 2000 | 10000 | 1/5 | 98.8 |
| 14 | | 2000 | 24000 | 1/12 | 99.1 |
| 15 | | 2000 | 30000 | 1/15 | 99.0 |
| 16 | | 2000 | 60000 | 1/30 | 99.1 |
| 17 | | 2000 | 0 | | 56.5 |
| 18 | | 0 | 0 | | 0 |

Example 16

The same test as the one effected in Example 12 was carried out by using a Roundup liquid formulation as a herbicide and the enhancers 30 and 43 listed in Example 12 each in a dose as specified in Table 16. Table 16 shows the results.

TABLE 16

| Test no. | Enhancer | Herbicide content (ppm) | Enhancer content (ppm) | Herbicide/ enhancer weight ratio | Herbicidal ratio (%) |
|---|---|---|---|---|---|
| 1 | Enhancer | 2000 | 200 | 1/0.1 | 75.6 |
| 2 | 30 | 2000 | 1000 | 1/0.5 | 88.4 |
| 3 | | 2000 | 2000 | 1/1.0 | 93.8 |
| 4 | | 2000 | 10000 | 1/5 | 97.7 |
| 5 | | 2000 | 24000 | 1/12.0 | 99.1 |
| 6 | | 2000 | 60000 | 1/30 | 99.3 |
| 7 | | 2000 | 80000 | 1/40 | 99.2 |
| 8 | | 2000 | 0 | | 56.5 |
| 9 | | 0 | 0 | | 0 |
| 10 | Enhancer | 2000 | 200 | 1/0.1 | 78.5 |
| 11 | 43 | 2000 | 1000 | 1/0.5 | 93.4 |
| 12 | | 2000 | 2000 | 1/1.0 | 99.1 |

TABLE 16-continued

| Test no. | Enhancer | Herbicide content (ppm) | Enhancer content (ppm) | Herbicide/ enhancer weight ratio | Herbicidal ratio (%) |
|---|---|---|---|---|---|
| 13 | | 2000 | 10000 | 1/5 | 98.9 |
| 14 | | 2000 | 24000 | 1/12.0 | 99.2 |
| 15 | | 2000 | 60000 | 1/30 | 99.1 |
| 16 | | 2000 | 80000 | 1/40 | 98.1 |
| 17 | | 2000 | 0 | | 56.5 |
| 18 | | 0 | 0 | | 0 |

Example 17

The same test as the one effected in Example 12 was carried out by using a Roundup liquid formulation as a herbicide and the enhancers 26 and 39 listed in Example 12 each in a dose as specified in Table 17. Table 17 shows the results.

TABLE 17

| Test no. | Enhancer | Herbicide content (ppm) | Enhancer content (ppm) | Herbicide/ enhancer weight ratio | Herbicidal ratio (%) |
|---|---|---|---|---|---|
| 1 | Enhancer 26 | 2000 | 200 | 1/0.1 | 81.5 |
| 2 | | 2000 | 1000 | 1/0.5 | 94.3 |
| 3 | | 2000 | 2000 | 1/1.0 | 98.2 |
| 4 | | 2000 | 10000 | 1/5 | 98.9 |
| 5 | | 2000 | 24000 | 1/12 | 99.2 |
| 6 | | 2000 | 30000 | 1/15 | 99.0 |
| 7 | | 2000 | 80000 | 1/40 | 99.1 |
| 8 | | 2000 | 0 | | 56.5 |
| 9 | | 0 | 0 | | 0 |
| 10 | Enhancer 39 | 2000 | 200 | 1/0.1 | 83.2 |
| 11 | | 2000 | 1000 | 1/0.5 | 95.5 |
| 12 | | 2000 | 2000 | 1/1.0 | 99.1 |
| 13 | | 2000 | 10000 | 1/5 | 99.0 |
| 14 | | 2000 | 24000 | 1/12 | 89.9 |
| 15 | | 2000 | 30000 | 1/15 | 99.0 |
| 16 | | 2000 | 80000 | 1/40 | 99.1 |
| 17 | | 2000 | 0 | | 56.5 |
| 18 | | 0 | 0 | | 0 |

Example 18

The same test as the one effected in Example 14 was carried out by using a Sumithion emulsion as an insecticide and the enhancers 25 and 38 listed in Example 12 each in a dose as specified in Table 18. Table 18 shows the results.

TABLE 18

| Test no. | Enhancer | Insecticide content (ppm) | Enhancer content (ppm) | Insecticide/ enhancer weight ratio | Insecticidal ratio (%) |
|---|---|---|---|---|---|
| 1 | Enhancer 25 | 250 | 25 | 1/0.1 | 83.3 |
| 2 | | 250 | 125 | 1/0.5 | 93.3 |
| 3 | | 250 | 250 | 1/1.0 | 93.3 |
| 4 | | 250 | 500 | 1/2.0 | 100 |
| 5 | | 250 | 1000 | 1/4.0 | 100 |
| 6 | | 250 | 2500 | 1/10 | 100 |
| 7 | | 250 | 5000 | 1/20 | 100 |
| 8 | | 250 | 0 | | 46.7 |
| 9 | | 0 | 0 | | 0 |
| 10 | Enhancer 38 | 250 | 25 | 1/0.1 | 83.3 |
| 11 | | 250 | 125 | 1/0.5 | 93.3 |
| 12 | | 250 | 250 | 1/1.0 | 100 |
| 13 | | 250 | 500 | 1/2.0 | 100 |
| 14 | | 250 | 1000 | 1/4.0 | 100 |
| 15 | | 250 | 2500 | 1/10 | 100 |
| 16 | | 250 | 5000 | 1/20 | 100 |
| 17 | | 250 | 0 | | 46.7 |
| 18 | | 0 | 0 | | 0 |

Example 19

The same test as the one effected in Example 13 was carried out by using an Osadan wettable powder as an acaricide and the enhancers 29 and 42 listed in Example 12 each in a dose as specified in Table 19. Table 19 shows the results.

TABLE 19

| Test no. | Enhancer | Acaricide content (ppm) | Enhancer content (ppm) | Acaricide/ enhancer weight ratio | Acaricidal ratio (%) |
|---|---|---|---|---|---|
| 1 | Enhancer 29 | 100 | 10 | 1/0.1 | 77.8 |
| 2 | | 100 | 50 | 1/0.5 | 91.1 |
| 3 | | 100 | 100 | 1/1.0 | 91.1 |
| 4 | | 100 | 200 | 1/2.0 | 100 |
| 5 | | 100 | 1000 | 1/10 | 100 |
| 6 | | 100 | 1500 | 1/15 | 100 |
| 7 | | 100 | 2000 | 1/20 | 100 |
| 8 | | 100 | 0 | | 52.3 |
| 9 | | 0 | 0 | | 2.2 |
| 10 | Enhancer 42 | 100 | 10 | 1/0.1 | 77.8 |
| 11 | | 100 | 50 | 1/0.5 | 94.4 |
| 12 | | 100 | 100 | 1/1.0 | 94.4 |
| 13 | | 100 | 200 | 1/2.0 | 100 |
| 14 | | 100 | 1000 | 1/10 | 100 |
| 15 | | 100 | 1500 | 1/15 | 100 |
| 16 | | 100 | 2000 | 1/20 | 100 |
| 17 | | 100 | 0 | | 52.3 |
| 18 | | 0 | 0 | | 2.2 |

Example 20

The same test as the one effected in Example 13 was carried out by using an Osadan wettable powder as an acaricide and the enhancers 31 and 44 listed in Example 12 each in a dose as specified in Table 20. Table 20 shows the results.

TABLE 20

| Test no. | Enhancer | Acaricide content (ppm) | Enhancer content (ppm) | Acaricide/ enhancer weight ratio | Acaricidal ratio (%) |
|---|---|---|---|---|---|
| 1 | Enhancer 31 | 100 | 10 | 1/0.1 | 66.7 |
| 2 | | 100 | 50 | 1/0.5 | 83.3 |
| 3 | | 100 | 100 | 1/1.0 | 97.8 |
| 4 | | 100 | 200 | 1/2.0 | 100 |
| 5 | | 100 | 1000 | 1/10 | 100 |
| 6 | | 100 | 1500 | 1/15 | 100 |
| 7 | | 100 | 2000 | 1/20 | 100 |
| 8 | | 100 | 0 | | 52.3 |
| 9 | | 0 | 0 | | 0 |
| 10 | Enhancer 44 | 100 | 10 | 1/0.1 | 75.6 |
| 11 | | 100 | 50 | 1/0.5 | 88.9 |
| 12 | | 100 | 200 | 1/2.0 | 94.4 |

TABLE 20-continued

| Test no. | Enhancer | Acaricide content (ppm) | Enhancer content (ppm) | Acaricide/ enhancer weight ratio | Acaricidal ratio (%) |
|---|---|---|---|---|---|
| 13 | | 100 | 1000 | 1/10 | 100 |
| 14 | | 100 | 0 | | 52.3 |
| 15 | | 0 | 0 | | 0 |

Production Example 3

A four-neck flask provided with a stirrer, a thermometer and a dehydrating tube was charged with 66 g of N-(2-hydroxyethyl)-N-methyl-1,3-propylenediamine, which had been synthesized from an adduct of N-methylethanolamine with acrylonitrile in accordance with a known method [see J. Org. Chem., 26, 3409 (1960)], and 284 g of stearic acid. The mixture was heated to 180° C. and maintained at this temperature for about 10 hours while distilling off the water thus formed. Then 300 g of the product thus obtained was dissolved in 60 g of isopropyl alcohol and fed into an autoclave provided with a stirrer, a thermometer and a pressure gauge. After injecting 28 g of methyl chloride thereinto, the mixture was reacted at 100° C. for about 8 hours. After distilling off the isopropyl alcohol under reduced pressure, 320 g of the target compound was obtained. Based on the NMR and IR spectra, it was confirmed that this product had the following chemical structure. This compound will be referred to as the enhancer 47 hereinafter.

$$CH_3-\overset{\overset{\displaystyle CH_3}{|}}{\underset{\underset{\displaystyle CH_2CH_2OCC_{17}H_{35}}{\underset{\displaystyle \parallel}{|}}}{N^{\oplus}}}-CH_2CH_2CH_2NHCC_{17}H_{35}.Cl^{\ominus}$$
$$\phantom{CH_3-N^{\oplus}-CH_2CH_2CH_2NHCC_{17}H_{35}.Cl^{\ominus}\ \ }O$$

Example 21

The same test as the one effected in Example 1 was carried out, except that the enhancer 47 obtained in Production Example 3 and, the following enhancers 48 to 74 were used to prepare agricultural chemical compositions. Table 21 summarizes the results.

Enhancer 48; enhancer 47/Emulgen 909 [POE(9) nonyl phenol ether]=80/20.

Enhancer 49; enhancer 47/Emulgen 103 [POE(3) $C_{12}H_{25}OH$]=80/20.

Enhancer 50; enhancer 47/Emanon 4110 [POE(10) $C_{17}H_{35}COO$ H]=80/20.

Enhancer 51; enhancer 47/Rheodol TWL-120 [POE(20) $C_{11}H_{23}COO$ sorbitan ester]=80/20.

Enhancer 52; a compound represented by the following formula was used:

$$CH_3-\overset{\overset{\displaystyle CH_3}{|}}{\underset{\underset{\displaystyle C_{12}H_{25}}{|}}{N^{\oplus}}}-C_2H_4-O-\overset{\overset{\displaystyle O}{\parallel}}{C}-C_{12}H_{25}.Cl^{\ominus}$$

Enhancer 53; enhancer 52/Emulgen 703 [a mixture of POE(3) $C_{12}H_{25}OH$ and POE(3) $C_{13}H_{27}OH$]=75/25.

Enhancer 54; enhancer 52/Emanon 1112 [POE(12) $C_{11}H_{23}COOH$]=75/25.

Enhancer 55; enhancer 52/Rheodol TWO-120 [POE(20) $C_{17}H_{33}COO$ sorbitan ester]=75/25.

Enhancer 56; didecyldimethylammonium chloride.

Enhancer 57; monolauryltrimethylammonium chloride.

Enhancer 58; dilauryldihydroxyethylammonium chloride.

Enhancer 59; trimethylcocoammonium chloride.

Enhancer 60; a compound represented by the following formula was used:

$$CH_3-\overset{\overset{\displaystyle CH_3}{|}}{\underset{\underset{\displaystyle C_2H_4-O-\overset{\overset{\displaystyle }{}}{\underset{\underset{\displaystyle O}{\parallel}}{C}}-C_{12}H_{25}}{|}}{N^{\oplus}}}-C_3H_6-\overset{\overset{\displaystyle O}{\parallel}}{N}HC-C_{12}H_{25}.Cl^{\ominus}$$

Enhancer 61; enhancer 80/Emulgen 909=80/20.

Enhancer 62; enhancer 80/Emulgen 103=80/20.

Enhancer 63; enhancer 80/Emanon 4110=80/20.

Enhancer 64; enhancer 60/Rheodol TWO-120=80/20.

Enhancer 65; a compound represented by the following formula was used:

$$CH_3-\overset{\overset{\displaystyle CH_3}{|}}{\underset{\underset{\displaystyle C_{12}H_{25}}{|}}{N^{\oplus}}}-C_3H_6-\overset{\overset{\displaystyle O}{\parallel}}{N}HC-C_{17}H_{35}.Cl^{\ominus}$$

Enhancer 66; enhancer 65/Emulgen 703=75/25.

Enhancer 67; enhancer 65/Emanon 1112=75/25.

Enhancer 68; enhancer 65/Rheodol TWO-120=75/25.

Enhancer 69; a compound represented by the following formula was used:

$$CH_3-\overset{\overset{\displaystyle CH_3}{|}}{\underset{\underset{\displaystyle CH_2CH_2O-\overset{\overset{\displaystyle }{}}{\underset{\underset{\displaystyle O}{\parallel}}{C}}-C_7H_{15}}{|}}{N^{\oplus}}}-CH_2CH_2CH_2-NH-\overset{\overset{\displaystyle O}{\parallel}}{C}-C_7H_{15}.Cl^{\ominus}$$

Enhancer 70; enhancer 69/Emulgen 707 [POE(7) sec-$C_{12}$, $C_{13}$ ether]=75/25.

Enhancer 71; enhancer 69/Rheodol TWO-120=75/25.

Enhancer 72; a compound represented by the following formula was used:

$$CH_3-\overset{\overset{\displaystyle CH_3}{|}}{\underset{\underset{\displaystyle (CH_2CH_2O)_4-\overset{\overset{\displaystyle }{}}{\underset{\underset{\displaystyle O}{\parallel}}{C}}-C_7H_{15}}{|}}{N^{\oplus}}}-CH_2CH_2CH_2-NH-\overset{\overset{\displaystyle O}{\parallel}}{C}-C_{15}H_{31}.Cl^{\ominus}$$

Enhancer 73; enhancer 72/Emulgen 909=80/20.

Enhancer 74; enhancer 72/Rheodol TWO-120=80/20.

The expression "POE" as used herein is an abbreviation of "polyoxyethylene" and each value given in the parentheses is an average addition mole number of oxyethylene. In enhancer compositions, the composition ratio is by weight.

TABLE 21

| No. of enhancer | Herbicidal ratio (%) | | |
|---|---|---|---|
| | Karmex wettable powder | Herbiace water-soluble powder | Roundup liquid formulation |
| Invention product | | | |
| 47 | 97.8 | 97.6 | 99.1 |
| 48 | 97.5 | 99.1 | 99.0 |
| 49 | 99.1 | 99.1 | 99.0 |
| 50 | 99.2 | 98.5 | 97.5 |
| 51 | 99.0 | 98.5 | 98.9 |
| 52 | 99.0 | 98.9 | 99.1 |
| 53 | 98.5 | 99.1 | 99.1 |
| 54 | 98.9 | 98.6 | 98.7 |
| 55 | 99.1 | 99.2 | 99.3 |
| Comparative product | | | |
| 56 | 63.5 | 70.0 | 69.5 |
| 57 | 44.5 | 72.2 | 70.0 |
| 58 | 60.3 | 70.1 | 71.1 |
| 59 | 50.3 | 67.8 | 70.5 |
| Invention product | | | |
| 60 | 99.3 | 98.7 | 98.7 |
| 61 | 98.5 | 99.3 | 98.7 |
| 61 | 98.5 | 99.1 | 99.0 |
| 63 | 98.9 | 99.0 | 99.0 |
| 64 | 98.9 | 98.7 | 98.8 |
| 65 | 99.3 | 98.3 | 98.8 |
| 66 | 99.2 | 98.5 | 98.8 |
| 67 | 99.4 | 98.2 | 99.3 |
| 68 | 98.9 | 98.5 | 99.2 |
| 69 | 99.7 | 99.5 | 99.3 |
| 70 | 99.1 | 99.2 | 99.0 |
| 71 | 99.2 | 99.1 | 99.1 |
| 72 | 98.2 | 97.3 | 98.9 |
| 73 | 99.1 | 97.8 | 99.2 |
| 74 | 97.6 | 98.5 | 97.9 |
| none | 18.4 | 67.5 | 68.5 |

Example 22

The same test as the one effected in Example 2 was carried out, except that the enhancers 47 to 74, which were employed in Example 21, were used to prepare agricultural chemical compositions. Table 22 shows the results.

TABLE 22

| | No. of enhancer | Acaricidal ratio (%) | |
|---|---|---|---|
| | | Nissorun V emulsion | Osadan wettable powder |
| Invention product | 47 | 98.8 | 100 |
| | 48 | 97.8 | 100 |
| | 49 | 98.8 | 100 |
| | 50 | 100 | 98.8 |
| | 51 | 100 | 98.8 |
| | 52 | 100 | 98.8 |
| | 53 | 100 | 97.8 |
| | 54 | 100 | 99.2 |
| | 55 | 97.8 | 100 |
| Comparative product | 56 | 50.0 | 52.2 |
| | 57 | 50.0 | 46.5 |
| | 58 | 48.9 | 52.2 |
| | 59 | 50.0 | 74.4 |
| Invention product | 60 | 97.8 | 97.8 |
| | 61 | 97.8 | 98.8 |

TABLE 22-continued

| No. of enhancer | Acaricidal ratio (%) | |
|---|---|---|
| | Nissorun V emulsion | Osadan wettable powder |
| 62 | 98.8 | 100 |
| 63 | 100 | 100 |
| 64 | 100 | 100 |
| 65 | 100 | 100 |
| 66 | 100 | 97.8 |
| 67 | 100 | 98.8 |
| 68 | 100 | 97.8 |
| 69 | 100 | 98.9 |
| 70 | 99.4 | 100 |
| 71 | 100 | 100 |
| 72 | 96.7 | 97.8 |
| 73 | 100 | 96.7 |
| 74 | 93.3 | 95.6 |
| none | 44.4 | 38.9 |

Example 23

The same test as the one effected in Example 3 was carried out, except that the enhancers 47 to 74, which were employed in Example 21, were used to prepare agricultural chemical compositions. Table 23 shows the results.

TABLE 23

| | No. of enhancer | Insecticidal ratio (%) | |
|---|---|---|---|
| | | Sumithion emulsion | Malathion emulsion |
| Invention product | 47 | 90.0 | 90.0 |
| | 48 | 100 | 100 |
| | 49 | 93.3 | 93.3 |
| | 50 | 93.3 | 96.7 |
| | 51 | 93.3 | 96.7 |
| | 52 | 90.0 | 90.0 |
| | 53 | 100 | 100 |
| | 54 | 100 | 100 |
| | 55 | 100 | 100 |
| Comparative product | 56 | 60.0 | 50.0 |
| | 57 | 50.0 | 53.3 |
| | 58 | 53.3 | 60.0 |
| | 59 | 40.0 | 43.3 |
| Invention product | 60 | 100 | 100 |
| | 61 | 93.3 | 100 |
| | 62 | 93.3 | 96.7 |
| | 63 | 96.7 | 93.3 |
| | 64 | 100 | 100 |
| | 65 | 100 | 96.7 |
| | 66 | 100 | 100 |
| | 67 | 93.3 | 100 |
| | 68 | 93.3 | 93.3 |
| | 69 | 95.5 | 97.8 |
| | 70 | 100 | 100 |
| | 71 | 100 | 100 |
| | 72 | 93.3 | 100 |
| | 73 | 100 | 96.7 |
| | 74 | 93.3 | 93.3 |
| control lot | | 40.0 | 50.0 |

Examples 21, 22 and 23 show the tests wherein the efficacies of the enhancers for agricultural chemicals according to the present invention were compared with those of common cationic surfactants (comparative products) as enhancers for agricultural chemicals. As Tables 21 to 23 clearly indicate, the enhancers for agricultural chemicals of the present invention exerted remarkable effects and thus were usable on a practical level. In contrast, the comparative products somewhat enhanced the efficacies of the agricultural chemicals but were not effective on a practical level. Accordingly, it is observed that the enhancers for agricultural chemicals of the present invention would specifically enhance the efficacies of agricultural chemicals as compared with common cationic surfactants.

Example 24

The same test as the one effected in Example 21 was carried out by using a Roundup liquid formulation as a herbicide and the enhancers 47 and 60 listed in Example 21 each in a dose as specified in Table 24. Table 24 shows the results.

TABLE 24

| Test no. | Enhancer | Herbicide content (ppm) | Enhancer content (ppm) | Herbicide/ enhancer weight ratio | Herbicidal ratio (%) |
|---|---|---|---|---|---|
| 1 | Enhancer | 2000 | 200 | 1/0.1 | 82.3 |
| 2 | 47 | 2000 | 1000 | 1/0.5 | 95.5 |
| 3 | | 2000 | 2000 | 1/1.0 | 97.8 |
| 4 | | 2000 | 10000 | 1/5 | 98.9 |
| 5 | | 2000 | 24000 | 1/12 | 99.3 |
| 6 | | 2000 | 30000 | 1/15 | 99.0 |
| 7 | | 2000 | 60000 | 1/30 | 99.1 |
| 8 | | 2000 | 0 | | 50.6 |
| 9 | | 0 | 0 | | 0 |
| 10 | Enhancer | 2000 | 200 | 1/0.1 | 85.5 |
| 11 | 60 | 2000 | 1000 | 1/0.5 | 98.5 |
| 12 | | 2000 | 2000 | 1/1.0 | 98.9 |
| 13 | | 2000 | 10000 | 1/5 | 98.7 |
| 14 | | 2000 | 24000 | 1/12 | 99.3 |
| 15 | | 2000 | 30000 | 1/15 | 99.1 |
| 16 | | 2000 | 60000 | 1/30 | 98.8 |
| 17 | | 0 | 0 | | 0 |

Example 25

The same test as the one effected in Example 21 was carried out by using a Roundup liquid formulation as a herbicide and the enhancers 52 and 65 listed in Example 21 each in a dose as specified in Table 25. Table 25 shows the results.

TABLE 25

| Test no. | Enhancer | Herbicide content (ppm) | Enhancer content (ppm) | Herbicide/ enhancer weight ratio | Herbicidal ratio (%) |
|---|---|---|---|---|---|
| 1 | Enhancer | 2000 | 200 | 1/0.1 | 74.5 |
| 2 | 52 | 2000 | 1000 | 1/0.5 | 90.0 |
| 3 | | 2000 | 2000 | 1/1.0 | 99.0 |
| 4 | | 2000 | 10000 | 1/5 | 98.1 |
| 5 | | 2000 | 24000 | 1/12.0 | 99.3 |
| 6 | | 2000 | 60000 | 1/30 | 99.2 |
| 7 | | 2000 | 80000 | 1/40 | 99.1 |
| 8 | | 2000 | 0 | | 56.5 |
| 9 | | 0 | 0 | | 0 |
| 10 | Enhancer | 2000 | 200 | 1/0.1 | 83.5 |
| 11 | 65 | 2000 | 1000 | 1/0.5 | 95.6 |
| 12 | | 2000 | 2000 | 1/1.0 | 99.3 |
| 13 | | 2000 | 10000 | 1/5 | 99.0 |
| 14 | | 2000 | 24000 | 1/12.0 | 99.0 |
| 15 | | 2000 | 60000 | 1/30 | 98.9 |
| 16 | | 2000 | 80000 | 1/40 | 99.2 |
| 17 | | 2000 | 0 | | 56.5 |
| 18 | | 0 | 0 | | 0 |

Example 26

The same test as the one effected in Example 21 was carried out by using a Roundup liquid formulation as a herbicide and the enhancers 48 and 61 listed in Example 21 each in a dose as specified in Table 26. Table 26 shows the results.

TABLE 26

| Test no. | Enhancer | Herbicide content (ppm) | Enhancer content (ppm) | Herbicide/ enhancer weight ratio | Herbicidal ratio (%) |
|---|---|---|---|---|---|
| 1 | Enhancer | 2000 | 200 | 1/0.1 | 78.6 |
| 2 | 48 | 2000 | 1000 | 1/0.5 | 94.5 |
| 3 | | 2000 | 2000 | 1/1.0 | 98.0 |
| 4 | | 2000 | 10000 | 1/5 | 99.1 |
| 5 | | 2000 | 24000 | 1/12 | 99.0 |
| 6 | | 2000 | 30000 | 1/15 | 99.3 |
| 7 | | 2000 | 80000 | 1/40 | 99.1 |
| 8 | | 2000 | 0 | | 56.5 |
| 9 | | 0 | 0 | | 0 |
| 10 | Enhancer | 2000 | 200 | 1/0.1 | 83.2 |
| 11 | 61 | 2000 | 1000 | 1/0.5 | 95.1 |
| 12 | | 2000 | 2000 | 1/1.0 | 99.3 |
| 13 | | 2000 | 10000 | 1/5 | 99.0 |
| 14 | | 2000 | 24000 | 1/12 | 99.1 |
| 15 | | 2000 | 30000 | 1/15 | 99.2 |
| 16 | | 2000 | 80000 | 1/40 | 98.8 |
| 17 | | 2000 | 0 | | 56.5 |
| 18 | | 0 | 0 | | 0 |

Example 27

The same test as the one effected in Example 23 was carried out by using a Sumithion emulsion as an insecticide and the enhancers 47 and 60 listed in Example 21 each in a dose as specified in Table 27. Table 27 shows the results.

TABLE 27

| Test no. | Enhancer | Insecticide content (ppm) | Enhancer content (ppm) | Insecticide/ enhancer weight ratio | Insecticidal ratio (%) |
|---|---|---|---|---|---|
| 1 | Enhancer | 250 | 25 | 1/0.1 | 83.3 |
| 2 | 47 | 250 | 125 | 1/0.5 | 93.3 |
| 3 | | 250 | 250 | 1/1.0 | 100 |
| 4 | | 250 | 500 | 1/2.0 | 100 |
| 5 | | 250 | 1000 | 1/4.0 | 100 |
| 6 | | 250 | 2500 | 1/10 | 100 |
| 7 | | 250 | 5000 | 1/20 | 100 |
| 8 | | 250 | 0 | | 53.3 |
| 9 | | 0 | 0 | | 0 |
| 10 | Enhancer | 250 | 25 | 1/0.1 | 80.0 |
| 11 | 60 | 250 | 125 | 1/0.5 | 90.0 |
| 12 | | 250 | 250 | 1/1.0 | 100 |
| 13 | | 250 | 500 | 1/2.0 | 100 |
| 14 | | 250 | 1000 | 1/4.0 | 100 |
| 15 | | 250 | 2500 | 1/10 | 100 |
| 16 | | 250 | 5000 | 1/20 | 100 |
| 17 | | 250 | 0 | | 53.3 |
| 18 | | 0 | 0 | | 0 |

Example 28

The same test as the one effected in Example 22 was carried out by using an Osadan wettable powder as an acaricide and the enhancers 51 and 64 listed in Example 21 each in a dose as specified in Table 28. Table 28 shows the results.

TABLE 28

| Test no. | Enhancer | Acaricide content (ppm) | Enhancer content (ppm) | Acaricide/enhancer weight ratio | Acaricidal ratio (%) |
|---|---|---|---|---|---|
| 1 | Enhancer 51 | 100 | 10 | 1/0.1 | 83.3 |
| 2 | | 100 | 50 | 1/0.5 | 91.1 |
| 3 | | 100 | 100 | 1/1.0 | 100 |
| 4 | | 100 | 200 | 1/2.0 | 100 |
| 5 | | 100 | 1000 | 1/10 | 100 |
| 6 | | 100 | 1500 | 1/15 | 100 |
| 7 | | 100 | 2000 | 1/20 | 100 |
| 8 | | 100 | 0 | | 52.3 |
| 9 | | 0 | 0 | | 2.2 |
| 10 | Enhancer 64 | 100 | 10 | 1/0.1 | 77.8 |
| 11 | | 100 | 50 | 1/0.5 | 88.9 |
| 12 | | 100 | 100 | 1/1.0 | 94.4 |
| 13 | | 100 | 200 | 1/2.0 | 100 |
| 14 | | 100 | 1000 | 1/10 | 100 |
| 15 | | 100 | 1500 | 1/15 | 100 |
| 16 | | 100 | 2000 | 1/20 | 100 |
| 17 | | 100 | 0 | | 52.3 |
| 18 | | 0 | 0 | | 2.2 |

Example 29

The same test as the one effected in Example 22 was carried out by using an Osadan wettable powder as an acaricide and the enhancers 53 and 66 listed in Example 21 each in a dose as specified in Table 29. Table 29 shows the results.

TABLE 29

| Test no. | Enhancer | Acaricide content (ppm) | Enhancer content (ppm) | Acaricide/enhancer weight ratio | Acaricidal ratio (%) |
|---|---|---|---|---|---|
| 1 | Enhancer 53 | 100 | 10 | 1/0.1 | 68.9 |
| 2 | | 100 | 50 | 1/0.5 | 83.3 |
| 3 | | 100 | 100 | 1/1.0 | 94.4 |
| 4 | | 100 | 200 | 1/2.0 | 100 |
| 5 | | 100 | 1000 | 1/10 | 100 |
| 6 | | 100 | 1500 | 1/15 | 100 |
| 7 | | 100 | 2000 | 1/20 | 100 |
| 8 | | 100 | 0 | | 52.3 |
| 9 | | 0 | 0 | | 2.2 |
| 10 | Enhancer 66 | 100 | 10 | 1/0.1 | 72.2 |
| 11 | | 100 | 50 | 1/0.5 | 83.3 |
| 12 | | 100 | 200 | 1/2.0 | 100 |
| 13 | | 100 | 1000 | 1/10 | 100 |
| 14 | | 100 | 0 | | 52.3 |
| 15 | | 0 | 0 | | 2.2 |

Example 30

The same test as the one effected in Example 21 was carried out by using a Roundup liquid formulation as a herbicide and the enhancers 69 and 71 listed in Example 21 each in a dose as specified in Table 30. Table 30 shows the results.

TABLE 30

| Test no. | Enhancer | Herbicide content (ppm) | Enhancer content (ppm) | Herbicide/enhancer weight ratio | Herbicidal ratio (%) |
|---|---|---|---|---|---|
| 1 | Enhancer 69 | 2000 | 200 | 1/0.1 | 88.2 |
| 2 | | 2000 | 1000 | 1/0.5 | 95.6 |
| 3 | | 2000 | 2000 | 1/1.0 | 99.3 |
| 4 | | 2000 | 10000 | 1/5 | 99.2 |
| 5 | | 2000 | 24000 | 1/12 | 99.2 |
| 6 | | 2000 | 30000 | 1/15 | 99.3 |
| 7 | | 2000 | 60000 | 1/30 | 99.0 |
| 8 | | 2000 | 0 | | 56.5 |
| 9 | | 0 | 0 | | 0 |
| 10 | Enhancer 71 | 2000 | 200 | 1/0.1 | 90.4 |
| 11 | | 2000 | 1000 | 1/0.5 | 97.6 |
| 12 | | 2000 | 2000 | 1/1.0 | 98.5 |
| 13 | | 2000 | 10000 | 1/5 | 99.2 |
| 14 | | 2000 | 24000 | 1/12 | 99.0 |
| 15 | | 2000 | 30000 | 1/15 | 98.9 |
| 16 | | 2000 | 60000 | 1/30 | 99.0 |
| 17 | | 0 | 0 | | 0 |

Example 31

The same test as the one effected in Example 21 was carried out by using a Roundup liquid formulation as a herbicide and the enhancers 72 and 73 listed in Example 21 each in a dose as specified in Table 31. Table 31 shows the results.

TABLE 31

| Test no. | Enhancer | Herbicide content (ppm) | Enhancer content (ppm) | Herbicide/enhancer weight ratio | Herbicidal ratio (%) |
|---|---|---|---|---|---|
| 1 | Enhancer 72 | 2000 | 200 | 1/0.1 | 87.6 |
| 2 | | 2000 | 1000 | 1/0.5 | 89.2 |
| 3 | | 2000 | 2000 | 1/1.0 | 99.1 |
| 4 | | 2000 | 10000 | 1/5 | 98.6 |
| 5 | | 2000 | 24000 | 1/12 | 98.8 |
| 6 | | 2000 | 30000 | 1/15 | 97.5 |
| 7 | | 2000 | 60000 | 1/30 | 97.9 |
| 8 | | 2000 | 0 | | 56.5 |
| 9 | | 0 | 0 | | 0 |
| 10 | Enhancer 73 | 2000 | 200 | 1/0.1 | 85.6 |
| 11 | | 2000 | 1000 | 1/0.5 | 88.3 |
| 12 | | 2000 | 2000 | 1/1.0 | 97.6 |
| 13 | | 2000 | 10000 | 1/5 | 98.6 |
| 14 | | 2000 | 24000 | 1/12 | 99.0 |
| 15 | | 2000 | 30000 | 1/15 | 98.2 |
| 16 | | 2000 | 60000 | 1/30 | 98.8 |
| 17 | | 0 | 0 | | 0 |

Example 32

The same test as the one effected in Example 22 was carried out by using an Osadan wettable powder as an acaricide and the enhancers 69 and 70 listed in Example 21 each in a dose as specified in Table 32. Table 32 shows the results.

TABLE 32

| Test no. | Enhancer | Acaricide content (ppm) | Enhancer content (ppm) | Acaricide/enhancer weight ratio | Acaricidal ratio (%) |
|---|---|---|---|---|---|
| 1 | Enhancer 69 | 100 | 10 | 1/0.1 | 85.3 |
| 2 |  | 100 | 50 | 1/0.5 | 92.4 |
| 3 |  | 100 | 100 | 1/1.0 | 100 |
| 4 |  | 100 | 200 | 1/2.0 | 100 |
| 5 |  | 100 | 1000 | 1/10 | 100 |
| 6 |  | 100 | 1500 | 1/15 | 100 |
| 7 |  | 100 | 2000 | 1/20 | 100 |
| 8 |  | 100 | 0 |  | 52.3 |
| 9 |  | 0 | 0 |  | 2.2 |
| 10 | Enhancer 70 | 100 | 10 | 1/0.1 | 80.6 |
| 11 |  | 100 | 50 | 1/0.5 | 89.9 |
| 12 |  | 100 | 100 | 1/1.0 | 95.5 |
| 13 |  | 100 | 200 | 1/2.0 | 100 |
| 14 |  | 100 | 1000 | 1/10 | 100 |
| 15 |  | 100 | 1500 | 1/15 | 100 |
| 16 |  | 100 | 2000 | 1/20 | 100 |
| 17 |  | 100 | 0 |  | 52.3 |
| 18 |  | 0 | 0 |  | 2.2 |

TABLE 34

| Test no. | Enhancer | Insecticide content (ppm) | Enhancer content (ppm) | Insecticide/enhancer weight ratio | Insecticidal ratio (%) |
|---|---|---|---|---|---|
| 1 | Enhancer 69 | 250 | 25 | 1/0.1 | 82.5 |
| 2 |  | 250 | 125 | 1/0.5 | 96.1 |
| 3 |  | 250 | 250 | 1/1.0 | 100 |
| 4 |  | 250 | 500 | 1/2.0 | 100 |
| 5 |  | 250 | 1000 | 1/4.0 | 100 |
| 6 |  | 250 | 2500 | 1/10 | 100 |
| 7 |  | 250 | 5000 | 1/20 | 100 |
| 8 |  | 250 | 0 |  | 53.3 |
| 9 |  | 0 | 0 |  | 0 |
| 10 | Enhancer 71 | 250 | 25 | 1/0.1 | 89.2 |
| 11 |  | 250 | 125 | 1/0.5 | 98.0 |
| 12 |  | 250 | 250 | 1/1.0 | 100 |
| 13 |  | 250 | 500 | 1/2.0 | 100 |
| 14 |  | 250 | 1000 | 1/4.0 | 100 |
| 15 |  | 250 | 2500 | 1/10 | 100 |
| 16 |  | 250 | 5000 | 1/20 | 100 |
| 17 |  | 250 | 0 |  | 53.3 |
| 18 |  | 0 | 0 |  | 0 |

Example 33

The same test as the one effected in Example 22 was carried out by using an Osadan wettable powder as an acaricide and the enhancers 72 and 73 listed in Example 21 each in a dose as specified in Table 33. Table 33 shows the results.

TABLE 33

| Test no. | Enhancer | Acaricide content (ppm) | Enhancer content (ppm) | Acaricide/enhancer weight ratio | Acaricidal ratio (%) |
|---|---|---|---|---|---|
| 1 | Enhancer 72 | 100 | 10 | 1/0.1 | 93.3 |
| 2 |  | 100 | 50 | 1/0.5 | 97.8 |
| 3 |  | 100 | 100 | 1/1.0 | 100 |
| 4 |  | 100 | 200 | 1/2.0 | 100 |
| 5 |  | 100 | 1000 | 1/10 | 100 |
| 6 |  | 100 | 1500 | 1/15 | 100 |
| 7 |  | 100 | 2000 | 1/20 | 100 |
| 8 |  | 100 | 0 |  | 52.3 |
| 9 |  | 0 | 0 |  | 2.2 |
| 10 | Enhancer 73 | 100 | 10 | 1/0.1 | 92.2 |
| 11 |  | 100 | 50 | 1/0.5 | 96.7 |
| 12 |  | 100 | 100 | 1/1.0 | 98.9 |
| 13 |  | 100 | 200 | 1/2.0 | 100 |
| 14 |  | 100 | 1000 | 1/10 | 100 |
| 15 |  | 100 | 1500 | 1/15 | 100 |
| 16 |  | 100 | 2000 | 1/20 | 100 |
| 17 |  | 100 | 0 |  | 52.3 |
| 18 |  | 0 | 0 |  | 2.2 |

Example 34

The same test as the one effected in Example 23 was carried out by using a Sumithion emulsion as an insecticide and the enhancers 69 and 71 listed in Example 21 each in a dose as specified in Table 34. Table 34 shows the results.

Example 35

The same test as the one effected in Example 23 was carried out by using a Sumithion emulsion as an insecticide and the enhancers 72 and 78 listed in Example 21 each in a dose as specified in Table 35. Table 35 shows the results.

TABLE 35

| Test no. | Enhancer | Insecticide content (ppm) | Enhancer content (ppm) | Insecticide/enhancer weight ratio | Insecticidal ratio (%) |
|---|---|---|---|---|---|
| 1 | Enhancer 72 | 250 | 25 | 1/0.1 | 86.7 |
| 2 |  | 250 | 125 | 1/0.5 | 93.3 |
| 3 |  | 250 | 250 | 1/1.0 | 100 |
| 4 |  | 250 | 500 | 1/2.0 | 100 |
| 5 |  | 250 | 1000 | 1/4.0 | 100 |
| 6 |  | 250 | 2500 | 1/10 | 100 |
| 7 |  | 250 | 5000 | 1/20 | 100 |
| 8 |  | 250 | 0 |  | 53.3 |
| 9 |  | 0 | 0 |  | 0 |
| 10 | Enhancer 73 | 250 | 25 | 1/0.1 | 90.0 |
| 11 |  | 250 | 125 | 1/0.5 | 93.3 |
| 12 |  | 250 | 250 | 1/1.0 | 100 |
| 13 |  | 250 | 500 | 1/2.0 | 100 |
| 14 |  | 250 | 1000 | 1/4.0 | 100 |
| 15 |  | 250 | 2500 | 1/10 | 100 |
| 16 |  | 250 | 5000 | 1/20 | 100 |
| 17 |  | 250 | 0 |  | 53.3 |
| 18 |  | 0 | 0 |  | 0 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. An agricultural chemical composition comprising an agricultural chemical and an effective amount for enhancing the effectiveness of the agricultural chemical of an enhancer compound represented by the following general formula (III):

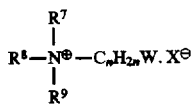 (III)

wherein
R$^7$ and R$^8$ are either the same or different from each other and each represents an alkyl group having 1 to 4 carbon atoms, an alkenyl group having 2 to 4 carbon atoms or

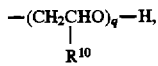

wherein q is 1 to 30 and R$^{10}$ or each of the plural R$^{10}$'s is a hydrogen atom or a methyl group;

R$_9$ represents an alkyl group having 6 to 36 carbon atoms,

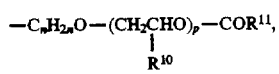

wherein n is 2 to 9, p is 0 to 30, R$^{11}$ is an alkyl group having 5 to 35 carbon atoms and R$^{10}$ is as described above, —C$_m$H$_{2m}$NH—COR$^{11}$ wherein m is 2 to 9 and R$^{11}$ is as described above or

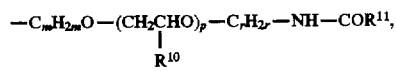

wherein r is 2 to 6 and m, p, R$^{10}$ and R$^{11}$ are described above;

W represents

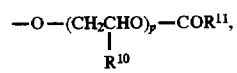

wherein p, R$^{10}$ and R$^{11}$ are described above, —NH—COR$^{11}$, wherein R$^{11}$ is as described above or

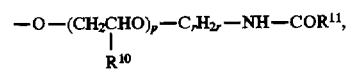

wherein p, r, R$^{10}$ and R$^{11}$ are as described above;

n is 2 to 9; and

X$^\ominus$ is a counter ion.

2. A method for enhancing the effectiveness of an agricultural chemical which comprises applying an enhancer compound represented by the following general formula (III) with an agricultural chemical to a locus which would benefit from such treatment:

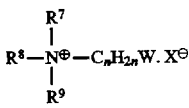 (III)

wherein R$^7$ and R$^8$ are either the same or different from each other and each represents an alkyl group having 1 to 4 carbon atoms, an alkenyl group having 2 to 4 carbon atoms or

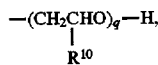

wherein q is 1 to 30 and R$^{10}$ or each of the plural R$^{10}$'s is a hydrogen atom or a methyl group;

represents an alkyl group having 6 to 36 carbon atoms,

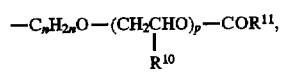

wherein n is 2 to 9, p is 0 to 30, R$^{11}$ is an alkyl group having 5 to 35 carbon atoms and R$^{10}$ is as described above, —C$_m$H$_{2m}$NH—COR$^{11}$, wherein m is 2 to 9 and R$^{11}$ is as described above, or

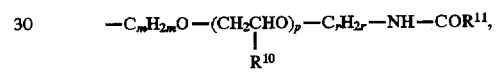

wherein r is 2 to 6 and m,
p, R$^{10}$ and R$^{11}$ are described above;

W represents

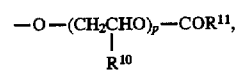

wherein p R$^{10}$ and R$^{11}$ are as described above, —NH—COR$^{11}$, wherein R$^{11}$ is as described above, or

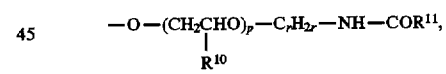

wherein p, r, R$^{10}$ and R$^{11}$ are as described above;

n is 2 to 9; and

X$^\ominus$ is a counter ion.

* * * * *

UNITED STATES PATENT AND TRADEMARK OFFICE
CERTIFICATE OF CORRECTION

PATENT NO. : 5,728,649
DATED : March 17, 1998
INVENTOR(S) : Hasebe et al.

It is certified that error appears in the above-indentified patent and that said Letters Patent is hereby corrected as shown below:

Please add the following new claims:

--36. The agricultural chemical composition as claimed in claim 31, wherein the weight ratio of the compound represented by formula (III) to the agricultural chemical is from 0.05 to 50.

37. The agricultural chemical composition as claimed in claim 31, wherein the weight ratio of the compound represented by formula (III) to the agricultural chemical is from 0.05 to 20.

38. The agricultural chemical composition as claimed in claim 31, wherein the weight ratio of the compound represented by formula (III) to the agricultural chemical is from 0.1 to 10.

UNITED STATES PATENT AND TRADEMARK OFFICE
CERTIFICATE OF CORRECTION

PATENT NO. : 5,728,649
DATED : March 17, 1998
INVENTOR(S) : Hasebe et al.

It is certified that error appears in the above-indentified patent and that said Letters Patent is hereby corrected as shown below:

39. The agricultural chemical composition as claimed in claim 31, which further comprises a surfactant other than the compound represented by the formula (III).

40. The agricultural chemical composition as claimed in claim 6, wherein the surfactant is a nonionic surfactant.

41. The agricultural chemical composition as claimed in claim 31, wherein the weight ratio of the compound represented by formula (III) to the surfactant other than the compound represented by the formula (III) is from 1/10 to 50/1.

42. The method as claimed in claim 32, wherein the enhancer and the agricultural chemical are diluted with water or a liquid carrier before applying.

43. The method as claimed in claim 32, wherein a surfactant other than the compound represented by the formula (III) is further applied.

UNITED STATES PATENT AND TRADEMARK OFFICE
CERTIFICATE OF CORRECTION

PATENT NO. : 5,728,649
DATED : March 17, 1998
INVENTOR(S) : Hasebe et al.

It is certified that error appears in the above-indentified patent and that said Letters Patent is hereby corrected as shown below:

44. The method as claimed in claim 32, wherein the surfactant is a nonionic surfactant.

45. The method as claimed in claim 43, wherein the weight ratio of the compound represented by formula (III) to the surfactant other than the compound represented by the formula (III) is from 1/10 to 50/1.

46. The method as claimed in claim 32, wherein the weight ratio of the compound represented by formula (III) to the agricultural chemical is from 0.05 to 50.

UNITED STATES PATENT AND TRADEMARK OFFICE
CERTIFICATE OF CORRECTION

PATENT NO. : 5,728,649
DATED : March 17, 1998
INVENTOR(S) : Hasebe et al.

It is certified that error appears in the above-indentified patent and that said Letters Patent is hereby corrected as shown below:

47. The method as claimed in claim 32, wherein the weight ratio of the compound represented by formula (III) to the agricultural chemical is from 0.05 to 20.

48. The method as claimed in claim 32, wherein the weight ratio of the compound represented by formula (III) to the agricultural chemical is from 0.1 to 10.--

Signed and Sealed this

Nineteenth Day of October, 1999

Attest:

Attesting Officer

Q. TODD DICKINSON

Acting Commissioner of Patents and Trademarks